US011339117B2

(12) United States Patent
Luyken

(10) Patent No.: US 11,339,117 B2
(45) Date of Patent: May 24, 2022

(54) METHOD FOR THE PRODUCTION OF ETHYLENEAMINES

(71) Applicant: BASF SE, Ludwigshafen am Rhein (DE)

(72) Inventor: Hermann Luyken, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 203 days.

(21) Appl. No.: 16/759,347

(22) PCT Filed: Oct. 17, 2018

(86) PCT No.: PCT/EP2018/078320
§ 371 (c)(1),
(2) Date: Apr. 26, 2020

(87) PCT Pub. No.: WO2019/081283
PCT Pub. Date: May 2, 2019

(65) Prior Publication Data
US 2020/0308097 A1    Oct. 1, 2020

(30) Foreign Application Priority Data
Oct. 27, 2017 (EP) ................................. 17198943.7

(51) Int. Cl.
C07C 209/84 (2006.01)

(52) U.S. Cl.
CPC .................. *C07C 209/84* (2013.01)

(58) Field of Classification Search
CPC .................................................. C07C 209/84
See application file for complete search history.

(56) References Cited

U.S. PATENT DOCUMENTS

| | | | |
|---|---|---|---|
| 2,519,803 A | 8/1950 | Weber et al. | |
| 2,861,995 A | 11/1958 | MacKenzie | |
| 3,112,318 A | 11/1963 | Lemon et al. | |
| 3,137,730 A | 6/1964 | Fitz-William | |
| 3,270,059 A | 8/1966 | Winderl et al. | |
| 4,111,840 A | 9/1978 | Best | |
| 7,635,790 B2 | 12/2009 | van Cauwenberge et al. | |
| 7,700,806 B2 | 4/2010 | van Cauwenberge et al. | |
| 7,880,036 B2 | 2/2011 | Dahmen et al. | |
| 7,915,454 B2 | 3/2011 | Oftring et al. | |
| 7,919,655 B2 | 4/2011 | Kubanek et al. | |
| 8,163,139 B2 * | 4/2012 | Pickenacker | C07C 209/86 203/64 |
| 8,268,995 B2 | 9/2012 | Kubanek et al. | |
| 8,299,249 B2 | 10/2012 | Dahmen et al. | |
| 8,765,634 B2 | 7/2014 | Kubanek et al. | |
| 8,766,010 B2 | 7/2014 | Jödecke et al. | |
| 9,019,075 B2 | 4/2015 | Hayashida | |
| 9,828,329 B2 | 11/2017 | Luyken et al. | |

| | | | |
|---|---|---|---|
| 2007/0043217 A1 | 2/2007 | Siegert et al. | |
| 2020/0102262 A1 | 4/2020 | Bebensee et al. | |
| 2020/0131111 A1 | 4/2020 | Heidemann et al. | |

FOREIGN PATENT DOCUMENTS

| | | |
|---|---|---|
| CN | 102190588 A | 9/2011 |
| CN | 102233272 A | 11/2011 |
| CN | 106607060 A | 5/2017 |
| DE | 1154121 B | 9/1963 |

(Continued)

OTHER PUBLICATIONS

U.S. Appl. No. 16/620,023, Bebensee et al.
U.S. Appl. No. 16/759,346, filed Apr. 26, 2020, Luyken.
U.S. Appl. No. 16/759,347, filed Apr. 26, 2020, Luyken et al.
U.S. Appl. No. 16/759,348, filed Apr. 26, 2020, Luyken et al.
U.S. Appl. No. 16/759,428, filed Apr. 27, 2020, Luyken.
Arné, M., "Alkyl Amines", Process Economics Program, Report No. 138, SRI International, Mar. 1981, entire report.
European Search Report for EP Patent Application No. 17198933.8 dated Apr. 10, 2018.
European Search Report for EP Patent Application No. 17198935.3 dated Apr. 18, 2018.
European Search Report for EP Patent Application No. 17198939.5 dated Apr. 10, 2018.

(Continued)

*Primary Examiner* — Yong L Chu
(74) *Attorney, Agent, or Firm* — Faegre Drinker Biddle & Reath LLP

(57) ABSTRACT

The present invention relates to a process for purifying a mixture comprising MEG, MEA, EDA and DETA, and low boilers having a boiling point not higher than PIP and high boilers having a boiling point not lower than AEEA, wherein the process comprises the following steps:
 a) separating a mixture comprising MEG, MEA, EDA and DETA, and low boilers having a boiling point not higher than PIP and high boilers having a boiling point not lower than AEEA, into
  (i) a mixture A comprising EDA and the low boilers having a boiling point not higher than PIP; and
  (ii) a mixture B comprising MEA; and
  (iii) a mixture C comprising MEG, DETA and the high boilers having a boiling point not lower than AEEA;
 b) separating mixture C from stage a) into
  (i) a mixture D comprising MEG; and
  (ii) a mixture E comprising MEG, DETA and the high boilers having a boiling point not lower than AEEA;
 c) separating mixture E from stage b) either into
  (i) a mixture F comprising MEG and DETA; and
  (ii) a mixture G comprising the high boilers having a boiling point not lower than AEEA;
  or into
  (i) a mixture F comprising MEG and DETA; and
  (ii) a mixture G1 comprising AEEA; and
  (iii) a mixture G2 comprising the high boilers having a boiling point higher than AEEA;
 d) separating mixture F from stage c) by extractive distillation with triethylene glycol into
  (i) a mixture H comprising MEG; and
  (ii) a mixture I comprising DETA and TEG.

17 Claims, 4 Drawing Sheets

(56) References Cited

FOREIGN PATENT DOCUMENTS

| | | |
|---|---|---|
| DE | 1172268 B | 6/1964 |
| EP | 2346809 A1 | 7/2011 |
| EP | 2487151 A1 | 8/2012 |
| EP | 2507202 A1 | 10/2012 |
| WO | WO-200537769 A1 | 4/2005 |
| WO | WO-2007093514 A1 | 8/2007 |
| WO | WO-2007093552 A1 | 8/2007 |
| WO | WO-2007093555 A1 | 8/2007 |
| WO | WO-2008006749 A1 | 1/2008 |
| WO | WO-2008006750 A1 | 1/2008 |
| WO | WO-2008104552 A1 | 9/2008 |
| WO | WO-2008104582 A2 | 9/2008 |
| WO | WO-2008104592 A1 | 9/2008 |
| WO | WO-2009008051 A1 | 1/2009 |
| WO | WO-2009080508 A1 | 7/2009 |
| WO | WO-2010042158 A1 | 4/2010 |
| WO | WO-2011067226 A1 | 6/2011 |
| WO | WO-2013072289 A1 | 5/2013 |
| WO | WO-2015135971 A1 | 9/2015 |

OTHER PUBLICATIONS

European Search Report for EP Patent Application No. 17198943.7 dated Apr. 18, 2018.

Ihmels, C., "Reaktionskinetische Untersuchungen zur metallkatalysierten Aminierung von Ethylenglykol in der flüssigen Phase", Diplomstudiengang Chemie, University of Oldenburg, Mar. 17, 2000, entire document.

International Preliminary Examination Report for PCT/EP2018/078322 dated Sep. 20, 2019.

International Preliminary Examination Report for PCT/EP2018/078326 dated Sep. 20, 2019.

International Search Report for PCT/EP2018/078320 dated Jan. 23, 2019.

International Search Report for PCT/EP2018/078322 dated Dec. 20, 2018.

International Search Report for PCT/EP2018/078324 datedDec. 14, 2018.

International Search Report for PCT/EP2018/078326 dated Dec. 7, 2018.

Roose, et al., "Amines, Aliphatic", Ullmann's Encyclopedia of Industrial Chemistry, vol. 7, Sep. 30, 2015, pp. 1-55.

Written Opinion of the International Searching Authority for PCT/EP2018/078320 dated Jan. 23, 2019.

Written Opinion of the International Searching Authority for PCT/EP2018/078322 dated Dec. 20, 2018.

Written Opinion of the International Searching Authority for PCT/EP2018/078324 dated Dec. 14, 2018.

Written Opinion of the International Searching Authority for PCT/EP2018/078326 dated Dec. 7, 2018.

* cited by examiner

METHOD FOR THE PRODUCTION OF ETHYLENEAMINES

CROSS-REFERENCE TO RELATED APPLICATIONS

This application is a national stage application (under 35 U.S.C. § 371) of PCT/EP2018/078320, filed Oct. 17, 2018, which claims benefit of European Application No. 17198943.7, filed Oct. 27, 2017, both of which are incorporated herein by reference in their entirety.

The present invention relates to a process for preparing ethanolamines and/or ethyleneamines proceeding from monoethylene glycol.

Two processes are generally employed for industrial scale preparation of ethylenediamine (FDA).

Firstly, EDA can be prepared by reaction of 1,2-dichloroethane with ammonia with elimination of HCl (EDC process). A further industrial scale process for preparation of EDA is the reaction of monoethanolamine (MEA) with ammonia in the presence of amination catalysts (MEA process).

As an alternative to the established processes, EDA can also be prepared by reaction of monoethylene glycol (MEG) with ammonia.

Such a process would have various advantages. One advantage is the good availability of MEG compared to MEA.

MEA is prepared on the industrial scale by reaction of ethylene oxide (EO) and ammonia. What is generally formed is a reaction mixture comprising, as well as MEA, also higher ethanolamines such as diethanolamine (DEOA) and triethanolamine (TEOA). These by-products have to be separated from MEA by a separate distillation step. Ethylene oxide is a highly flammable gas that can form explosive mixtures with air. The handling of EO is correspondingly complex. The preparation of MEA thus requires a technically complex EO plant with downstream purifying distillation.

By contrast, MEG can be produced either on the basis of petrochemical raw materials or on the basis of renewable raw materials. By petrochemical means, MEG is likewise prepared from EO by reaction with water. In the same way as in the reaction of EO with ammonia, it is not possible in the reaction of EO with water to prevent MEG that has already formed from reacting with EO to give by-products such as di- and triethylene glycol. The selectivity for MEG is about 90% and is thus, however, distinctly higher than the selectivity for MEA, which is generally 70-80%. The Shell omega process once again distinctly increased the selectivity for MEG—to about 99%. In the omega process, EO is reacted with $CO_2$ to give ethylene carbonate which, in the second step, is selectively hydrolyzed to MEG.

MEG can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal.

Alternatively, MEG can also be prepared from renewable raw materials, such as corn or sugarcane, by fermentation to ethanol, followed by dehydration to ethene and subsequent reaction with oxygen to give ethylene oxide.

Owing to the many production variants, the availability of MEG is generally high, which generally has a positive effect on raw material costs.

The prior art discloses that the reaction of MEG with ammonia to give EDA can be effected either in the liquid phase or in the gas phase.

The amination of MEG in the gas phase is disclosed in the two Chinese applications CN 102 190 588 and CN 102 233 272.

For instance, CN 102 190 588 describes the one-stage conversion of MEG and ammonia in the presence of Cu catalysts. According to the description, the reaction pressure is within a range from 3 to 30 bar. The reaction temperature is in the range from 150 to 350° C.

Application CN 102 233 272 discloses the reaction of MEG with ammonia in the gas phase over catalysts that include Cu and Ni as main constituents and Zr, Zn, Al, Ti, Mn and Ce as secondary component. However, the composition of the reaction mixtures obtained was not disclosed.

As an alternative to conversion in the gas phase, the reaction of MEG with ammonia and hydrogen can also be effected in the liquid phase. However, there is generally a considerable difference in the reaction characteristics of catalysts in the gas phase and liquid phase, and so it is generally impermissible to apply conclusions from the reaction characteristics of MEG in the gas phase to the reaction characteristics of MEG in the liquid phase.

An overview of the metal-catalyzed amination of MEG in the liquid phase is given in the Diplom thesis "Reaktionskinetische Untersuchungen zur metallkatalysierten Aminierung von Ethylenglykol in der flüssigen Phase" [Studies of Reaction Kinetics of the Metal-Catalyzed Amination of Ethylene Glycol in the Liquid Phase] by Carsten Wolfgang Ihmels ("Reaktionskinetische Untersuchungen zur metallkatalysierten Aminierung von Ethylenglykol in der flüssigen Phase", Diplom thesis from the Carl von Ossietzky University of Oldenburg dated Mar. 17, 2000). Ihmels describes a multitude of further reactions and side reactions that can occur in the amination of MEG, for example the formation of di- and triethanolamine, disproportionation, nitrile formation, carbonyl condensation and fragmentation reactions. Condensation and disproportionation in the case of dihydric alcohols can ultimately also lead to the formation of oligomers, such as diethylenetriamine (DETA), triethylenetetramine (TETA) and polymers. An important further side reaction is cyclization. For instance, diethanolamine or DETA can react further to give piperazine (PIP). Higher temperatures promote dehydrogenation, which follows on from the cyclization, to give aromatics. Thus, the reaction of MEG with ammonia gives a broad product spectrum, some products in the product spectrum being of greater commercial interest than others. For instance, the commercial demand for EDA, DETA and TETA is higher than that for PIP or aminoethylethanolamine (AEEA). The object of many studies in the reaction of MEG with ammonia was therefore to find catalysts and reaction conditions that lead to an advantageous product spectrum.

U.S. Pat. No. 4,111,840 discloses the reaction of MEG with ammonia and hydrogen at pressures of 500 to 5000 psig (about 34 to 340 bar) over supported Ni/Re catalysts. Supported silica/alumina catalysts having a surface area of 60 $m^2/g$ led to better results here than supported silica/alumina catalysts having a specific surface area of 150 $m^2/g$.

U.S. Pat. No. 3,137,730 discloses the reaction of MEG with ammonia in the liquid phase at temperatures of 200-300° C. and pressures above 1000 psig (about 69 bar) over Cu/Ni catalysts.

DE 1 172 268 discloses the conversion of ethylene glycol over catalysts comprising at least one of the metals Cu, Ag, Mn, Fe, Ni and Co. In one example, MEG was reacted with ammonia at 180° C. and a pressure of 300 bar in the presence of hydrogen over a Co catalyst.

Chinese application CN 106607060 A discloses catalysts for amination of MEG in the liquid phase.

WO 2007/093514 discloses a two-stage process for preparing EDA, wherein, in the first process stage, the amination is conducted over a hydroamination catalyst up to an MEA conversion of not more than 40% and, in the second process stage, a supported shaped Ru/Co catalyst body having small geometry is used and the second stage is conducted at a temperature at least 10° C. higher than the first process stage.

The product streams obtained in the processes described are generally separated by distillation to produce individual products in pure form, especially the particularly desired products EDA and DETA.

WO 2007/093555 discloses that the distillative workup of the reaction products from the MEG conversion is problematic since MEG and DETA form an azeotrope which is virtually independent of pressure and therefore cannot be separated by pressure swing distillation. According to WO 2007/093555, the azeotropic composition is about 44% by weight of MEG and 56% by weight of DETA and has a boiling point of 154° C. at 150 mbar, compared to the boiling point of pure MEG of 144° C. and of pure DETA of 142° C., in each case at the above-stated pressure of 150 mbar. WO 2007/093555 therefore discloses a process for distillatively separating a product stream from the MEG conversion, in which one stage of the separation sequence is conducted as an extractive distillation with triethylene glycol (TEG) from selective solvent for DETA. The disclosure discloses a separation sequence including the following steps:

Introducing the output from the MEG conversion into a first distillation unit K-I and separating the output introduced into a top stream comprising the ethylenediamine and piperazine components, and a bottom stream comprising the components having a boiling point greater than the boiling point of piperazine.

Introducing the bottom stream from column K-I into a second distillation column K-II and separating the bottom stream supplied into a top stream comprising monoethylene glycol, diethylenetriamine and monoethanolamine, and a bottom stream comprising components having a higher boiling point than monoethylene glycol and diethylenetriamine.

Feeding the top stream from column K-II into an extractive distillation column K-III which is fed, at the same separation stage or height, with triethylene glycol as selective solvent for diethylenetriamine, wherein a diethylenetriamine-laden stream comprising the selective triethylene glycol solvent is removed via the bottom, and a monoethylene glycol-comprising stream substantially free of diethylenetriamine is removed overhead in the extractive distillation column K-III.

The bottom stream from the extractive distillation column K-III, comprising DETA-laden selective solvent, is preferably fed to a desorption column K-IV, and separated therein into a DETA-comprising top stream and a TEG-comprising bottom stream. The TEG-comprising bottom stream from column K-IV is preferably recycled into the extractive distillation column K-III.

It was an object of the present invention to develop a process for purifying EDA which is prepared by reaction of MEG with ammonia, which makes it possible to obtain the desired EDA and DETA products in high purity, quality and yield. The process of the invention should additionally be combinable with other process stages to give an overall process in such a way that the combination of the process of the invention with the other process stages leads to advantages in the overall process.

For instance, the selectivity for the EDA and DETA target products in the overall process should be increased with respect to the selectivity for AEEA.

In addition, unconverted or partly converted products from the MEG conversion should be obtained in such a quality that they can be recycled back into the overall process in order to achieve a high overall yield based on the reactants used.

Moreover, the energy demand and the apparatus configuration of individual process stages should be reduced.

The object of the present invention was achieved by a process for purifying a mixture comprising MEG, MEA, EDA and DETA, and low boilers having a boiling point not higher than PIP and high boilers having a boiling point not lower than AEEA, wherein the process comprises the following steps:

a) separating a mixture comprising MEG, MEA, EDA and DETA, and low boilers having a boiling point not higher than PIP and high boilers having a boiling point not lower than AEEA, into
   (i) a mixture A comprising EDA and the low boilers having a boiling point not higher than PIP; and
   (ii) a mixture B comprising MEA; and
   (iii) a mixture C comprising MEG, DETA and the high boilers having a boiling point not lower than AEEA;
b) separating mixture C from stage a) into
   (i) a mixture D comprising MEG; and
   (ii) a mixture E comprising MEG, DETA and the high boilers having a boiling point not lower than AEEA;
c) separating mixture E from stage b) either into
   (i) a mixture F comprising MEG and DETA; and
   (ii) a mixture G comprising the high boilers having a boiling point not lower than AEEA;
   or
   (i) a mixture F comprising MEG and DETA; and
   (ii) a mixture G1 comprising AEEA; and
   (iii) a mixture G2 comprising the high boilers having a boiling point higher than AEEA;
d) separating mixture F from stage c) by extractive distillation with triethylene glycol into
   (i) a mixture H comprising MEG; and
   (ii) a mixture I comprising DETA and TEG.

The present process differs from the prior art in that MEA is additionally removed in stage a) and the process of the invention additionally comprises a stage b) in which excess MEG is removed.

The additional removal of MEA in stage a) enables the further reaction of MEA with ammonia in a separate reactor. Separate conversion of MEA can reduce the formation of AEEA, which is of lower commercial value than EDA and DETA.

The additional removal of MEG in stage b) enables introduction of the MEG reactant first into stage b) before it is converted in stage 1. This results in additional purification of the MEG before it is introduced into stage 1. In the context of the present invention, it has been recognized that, surprisingly, commercial MEG frequently comprises sulfur compounds and other by-products that reduce the service life of catalysts that are used in the MEG conversion. This may be true especially of MEG that is not of "fiber quality". In the MEG conversion (stage 1), the sulfur compounds in the MEG can reduce the service lives of the catalysts, the conversion and selectivity. As a result of the introduction of the MEG reactant into stage b), the unwanted impurities can be removed, which has a positive effect on the service lives of the catalysts and the selectivity and conversion in the MEG conversion.

A further advantage of the additional separation from MEG is that the stream introduced into the extractive distillation (stage d)) is smaller than in the process which is described in the prior art (WO 2007093555). The smaller flow rate that has to be separated in stage d) results in a smaller energy demand and lower thermal stress on the products. Thus, the process of the invention can give the desired DETA target product in a high quality. Moreover, owing to the smaller flow rate, the apparatus dimensions can be kept smaller, which can have a positive effect on the overall economic viability of the process.

The following abbreviations are used hereinafter:
AEEA: aminoethylethanolamine
AEP: aminoethylpiperazine
DETA: diethylenetriamine
EDA: ethylenediamine
EDC: ethylene dichloride
HEP: hydroxyethylpiperazine
HPA: heavy polyamine
MEA: monoethanolamine
MEG: monoethylene glycol
NM EDA: N-methylethylenediamine
PEHA: pentaethylenehexamines
PIP: piperazine
TEPA: tetraethylenepentamine
TETA: triethylenetetramine

A BRIEF DESCRIPTION OF THE FIGURES

Figure 1:
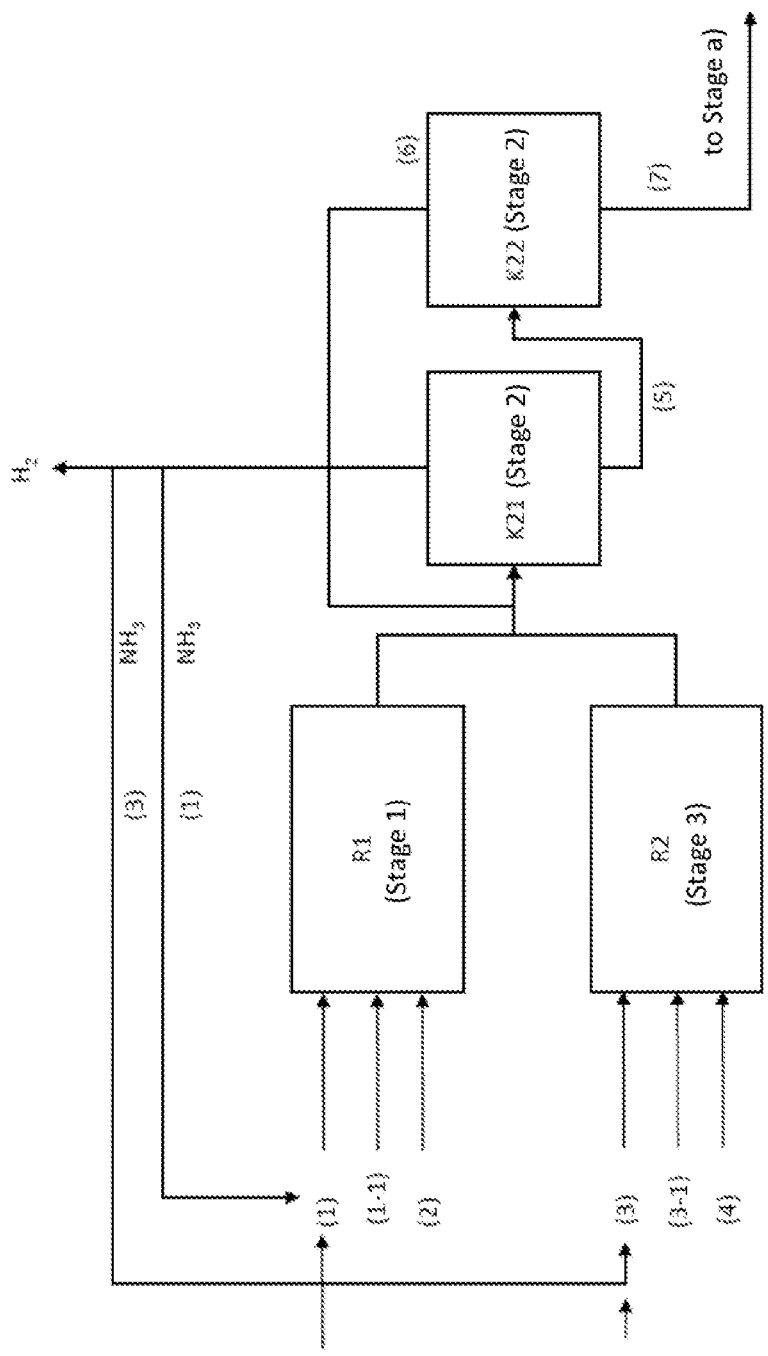
FIG. 1 illustrates the mixture comprising MEG, MEA, EDA and DETA was prepared in two parallel stages (stage 1: MEG conversion and stage 3: MEA conversion).

Unless specified otherwise, pressure figures relate to the absolute pressure figure.

The invention can be executed as follows.

A mixture (starting mixture) comprising MEG, MEA, EDA, DETA, low boilers having a boiling point not higher than PIP, and high boilers having a boiling point not lower than AEEA is introduced into the process of the invention.

The starting mixture is generally prepared by a reaction of MEG with ammonia (stage 1) to obtain a primary reaction mixture, and ammonia and/or hydrogen is separated from this primary reaction mixture in a further stage (stage 2).
MEG Conversion—Stage 1:
In a preferred embodiment, in a stage 1, MEG is converted in the presence of ammonia, hydrogen and a heterogeneous catalyst.
MEG Reactant
Ethylene glycol used is preferably industrial ethylene glycol having a purity of at least 98%, and most preferably ethylene glycol having a purity of at least 99% and most preferably of at least 99.5%.

The ethylene glycol used in the process can be prepared from ethylene obtainable from petrochemical processes. For instance, in general, ethene is oxidized in a first stage to ethylene oxide, which is subsequently reacted with water to give ethylene glycol. The ethylene oxide obtained can alternatively be reacted with carbon dioxide in what is called the omega process to give ethylene carbonate, which can then be hydrolyzed with water to give ethylene glycol. The omega process features a higher selectivity for ethylene glycol since fewer by-products, such as di- and triethylene glycol, are formed.

Ethene can alternatively be prepared from renewable raw materials. For instance, ethene can be formed by dehydration from bioethanol.

Ethylene glycol can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal.

It is possible to use an MEG which is not of "fiber quality" in the process of the invention. In this case, however, it is preferable to introduce the MEG together with mixture C into stage b) (as described below).
Sulfur Content in the MEG
Preferably, the MEG used comprises less than 100 ppm of sulfur. More preferably, the MEG used comprises less than 20 ppm of sulfur, most preferably less than 2 ppm of sulfur. Ideally, the MEG used does not comprise any sulfur at all. It is therefore advantageous to work up the freshly used MEG prior to introduction into the reaction section such that any sulfur present is removed. For this purpose, it is possible to introduce fresh MEG not directly into the MEG conversion (stage 1) but first into stage b) or stage 2 or stage a), preferably stage b), and, after the separation in stage b), recycle it into the MEG conversion (stage 1). It has been found that the rectification in the presence of amines not only removes any high boilers present in the fresh MEG but also any sulfur compounds present, such as sulfides, sulfites, mercaptans or thiols, which form adducts (high boilers) as a result of reaction or entrainment with the basic amines. The aforementioned preferred embodiments thus also enable the use of an MEG that is not of "fiber quality".

In a preferred embodiment, MEG, before being introduced into stage 1), is therefore first introduced into stage 2) or preferably into stage b), and the mixture D removed in stage b), which comprises the distilled MEG, is introduced into stage 1). The coupling of the MEG conversion (stage 1) with the process of the invention (stage b)) which is described in this embodiment thus enables the use of MEG that is not of fiber quality, since it has been found that, surprisingly, the sulfur content in stage b) can be lowered.
NH3 Reactant
Ethylene glycol is generally converted in the presence of ammonia.

The ammonia used may be conventional commercially available ammonia, for example ammonia with a content of more than 98% by weight of ammonia, preferably more than 99% by weight of ammonia, preferably more than 99.5% by weight, in particular more than 99.8% by weight of ammonia.
H2 Reactant
The process of the invention is preferably effected in the presence of hydrogen. The hydrogen is generally used in technical grade purity. The hydrogen can also be used in the form of a hydrogen-comprising gas, i.e. with additions of other inert gases, such as nitrogen, helium, neon, argon or carbon dioxide. Hydrogen-comprising gases used may, for example, be reformer offgases, refinery gases etc., if and as long as these gases do not comprise any catalyst poisons for the catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Amination Catalysts

MEG and ammonia are generally converted in the presence of amination catalysts.

Amination catalysts used may be any catalysts that bring about the conversion of MEG to EDA and/or MEA.

Preference is given to using amination catalysts comprising one or more active metals of groups 7 and/or 8 and/or 9 and/or 10 and/or 11 of the Periodic Table of the Elements. Examples of such active metals are Sn, Cu, Co, Ni and/or Fe, and also precious metals such as Rh, Ir, Ru, Pt, Pd, and Re.

The abovementioned active metals may be used in the process of the invention in the form of metal meshes or grids or in the form of Raney sponge or skeletal catalysts.

The amination catalysts may optionally comprise one or more added catalyst elements. The added catalyst elements are generally metals or semimetals selected from groups 1 to 6 and 12 to 17 of the Periodic Table of the Elements and the rare earth metals.

Preferred active metals are Co, Cu, Ni, Ru and Re. Very particularly preferred active metals are Ru, Co, Cu and Ni.

Preferred added catalyst elements are Zr, Al, Sb, Sn, Pb, Bi, In, Si, Ga, V, Nb, S, P, B, Cr, W, La, Ce, Y and Hf, more preferably Sn, P, Pb, Sb, La, Zr, Si and Al.

Particular preference is given to catalyst precursors comprising one or more active metals selected from the group consisting of Cu, Co, Ni and Ru, and optionally the added catalyst element Sn.

Particular preference is given to using amination catalysts which are prepared by reduction of what are called catalyst precursors.

In the catalyst precursor, the active metals and added catalyst elements are generally in the form of their oxygen compounds, for example of carbonates, oxides, mixed oxides or hydroxides of the active metals or added catalyst elements.

In general, the catalyst precursors are prepared by contacting soluble compounds of the active metals or of the added catalyst elements with a support material (impregnation) or by precipitation of the soluble compounds with a precipitant, where the precipitation can be effected in the presence of support material (called precipitative application) or in the absence of support materials (called mixed precipitation). The support materials that have been subjected to impregnation or precipitative application or the precipitates of the active metals or of the added catalyst elements, after drying, are generally converted to the oxygen compounds by calcination, where the conversion is generally effected by dewatering and/or breakdown.

The support material used may be the added catalyst element carbon, for example in the form of graphite, carbon black and/or activated carbon.

Preferred support materials are oxides of the added catalyst elements Al, Ti, Zn, Zr and Si or mixtures thereof, for example aluminum oxide (gamma, delta, theta, alpha, kappa, chi or mixtures thereof), titanium dioxide (anatase, rutile, brookite or mixtures thereof), zinc oxide, zirconium dioxide, silicon dioxide (such as silica, fumed silica, silica gel or silicates), aluminosilicates, minerals, such as hydrotalcite, chrysotile and sepiolite.

Particularly preferred support materials are aluminum oxide or zirconium oxide or mixtures thereof.

A particularly preferred support material is aluminum oxide.

The calcination is generally followed by a reduction of the catalyst precursors, wherein the catalyst precursor is converted to its catalytically active form.

After the reduction, the catalyst can be contacted with an oxygen-comprising gas stream such as air or a mixture of air with nitrogen.

This gives a passivated catalyst. The passivated catalyst generally has a protective oxide layer. This protective oxide layer simplifies the handling and storage of the catalyst, such that, for example, the installation of the passivated catalyst into the reactor is simplified.

Before being contacted with the reactants, a passivated catalyst is preferably reduced by treatment of the passivated catalyst with hydrogen or a hydrogen-comprising gas. The conditions in the activation generally correspond to the reduction conditions which are employed in the reduction. The activation generally removes the protective passivation layer.

The individual steps and methods for preparation of amination catalysts are known to those skilled in the art and can be found in the publications cited below.

Preference is given to using the following catalysts in the MEG conversion:

The Ni/Re catalysts disclosed in U.S. Pat. No. 4,111,840.

The Cu/Ni catalysts disclosed in U.S. Pat. No. 3,137,730.

The catalysts comprising at least one of the active metals Cu, Fe, Ni and Co that are disclosed in DE 1 172 268.

The supported Ru/Co catalysts disclosed in WO 2007/093514.

The catalysts comprising not only Al, Cu, Ni and Co but also the element Sn that are disclosed in WO 2013072289.

The catalysts including not only Zr and Ni but also Cu, Sn, Co and/or Fe and comprising, as further constituents, elements such as V, Nb, S, O, La, B, W, Pb, Sb, Bi and In that are disclosed in WO 200908051, WO 2009080508, WO 200006749 and WO 20008006750.

The catalysts disclosed in the applications with application number EP 1, EP 2 and EP 3.

Preference is given to using the catalyst in the form of small bodies, such as cylinders, spheres or tablets. The shaped bodies preferably have a diameter of not more than 10 mm, more preferably of not more than 5 mm, most preferably of not more than 2 mm.

Molar Ratio of the Reactants

Preferably, the reactant mixture used comprises a molar excess of ammonia based on the amount of MEG used. The molar NH3/MEG ratio may be 1 to 100, preferably 2 to 50, more preferably 7 to 18.

Reactors

Preferred reactors for the reaction of MEG with ammonia are generally tubular reactors. The amination catalyst is disposed in the tubular reactors preferably in the form of a moving bed or fixed bed.

Particular preference is given to reacting ethylene glycol and/or monoethanolamine with $NH_3$ in a tubular reactor in which the amination catalyst is disposed in the form of a fixed bed.

Alternatively, the reaction is advantageously effected in a shell and tube reactor or in a single-stream plant. In a single-stream plant, the tubular reactor in which the reaction is effected may consist of a series connection of a plurality of (e.g. two or three) individual tubular reactors. A possible and advantageous option here is the intermediate introduction of feed (comprising the reactant and/or ammonia and/or $H_2$) and/or cycle gas and/or reactor output from a downstream reactor.

It is also possible to keep the catalyst in the form of a suspension which is produced by movement of the liquid in a stirred tank, loop reactor or a fluidized bed.

Temperature and Pressure

The conversion of MEG is preferably effected at pressures of generally 5 to 50 MPa (50-500 bar), preferably 5 to 40 MPa, more preferably 20 to 35 MPa, and at temperatures of generally 50 to 350° C., particularly 100 to 300° C., preferably 120 to 270° C., more preferably 150 to 220° C., especially 170 to 200° C.

When the reactor is operated adiabatically, there is generally a rise in the temperature as a function of the conversion and the molar use ratio of MEG to ammonia. Thus, the adiabatic rise in temperature at the same conversion is lower when the amount of ammonia is higher. The rise in temperature in an adiabatic reactor is generally 0 to 200° C., preferably 5 to 100° C., more preferably 7 to 30° C.

The partial hydrogen pressure is preferably 0.25 to 20 MPa (2.5 to 200 bar), more preferably 0.5 to 15 MPa (5 to 150 bar), even more preferably 1 to 10 MPa (10 to 100 bar) and especially preferably 2 to 5 MPa (20 to 50 bar).

Catalyst Space Velocity

The catalyst space velocity, expressed as weight of MEG used per unit time divided by the weight of catalyst used, is 0.05 to 10 kg/kg h, preferably 0.1 to 5 kg/kg h, more preferably 0.2 to 1.5 kg/kg h.

Output

The output from the amination reactor generally comprises the products of the amination reaction, unconverted reactants, such as MEG and ammonia, and also hydrogen and water.

As products of the amination reaction, the output from the amination reactor also comprises the corresponding ethanolamines and/or ethyleneamines based on MEG.

More preferably, the reaction output comprises unconverted MEG, ammonia and hydrogen, and the reaction products MEA, EDA, PIP, AEEA, AEP, DETA and higher ethyleneamines (higher ethyleneamines refer to ethyleneamines having a boiling point not lower than TETA), for example TETA and TEPA.

In addition, the reaction output may comprise NMEDA. NMEDA is an unwanted by-product. In many industrial applications, a purity of EDA is specified where the proportion of NMEDA is below 500 ppm by weight. In a preferred embodiment, therefore, the process of the invention is combined with two further stages, a stage 4 (NMEDA removal) and a stage 5 (EDA purification), where the combination of the process stage makes it possible to obtain an on-spec EDA with low NMEDA content.

Ammonia Removal—Stage 2:

The mixtures from the MEG conversion generally comprise ammonia.

The amount of ammonia in the reaction outputs is typically in the range from 50% to 90% by weight, more preferably in the range from 60% to 85% by weight and most preferably in the range from 70 to 80% by weight.

Before the reaction outputs from stage 1 are used in the process of the invention, hydrogen and ammonia are typically separated from the mixtures obtained by the above-mentioned preparation processes in a stage 2.

Hydrogen and ammonia can be separated from the reaction mixture by methods known to those skilled in the art.

Preferably, the removal of ammonia and hydrogen is conducted by simple flashing, distillation or rectification.

This can be effected in flash vessels, distillation stills or rectification columns.

In the case of rectification, it is possible to use columns having a rectifying section and stripping section.

If the depletion of secondary components such as methylamine from the ammonia is required, the use of a rectifying section is advantageous.

Preference is given to using columns without a rectifying section since no reflux is required in that case, which reduces the energy demand of rectification.

The removal of hydrogen and ammonia can be conducted in a single stage at a particular pressure or in a staged manner in a series of setups in which the pressure is varied in order to match bottom and top temperatures such that they are practicable.

Preferably, ammonia and/or hydrogen are removed in one or more columns. Preferably, the pressure and composition at the top and bottom are chosen such that the condensation temperature is higher than 20° C., more preferably higher than 30° C., most preferably higher than 35° C. If the condensation temperature is within the ranges mentioned, the condenser can be cooled with cooling water which is generally at a temperature of 20-80° C., preferably 30 to 70° C. and more preferably 35-50° C.

The bottom temperature is preferably less than 250° C., more preferably less than 220° C., most preferably less than 200° C.

While the setting of the pressure is crucial for the setting of the temperatures, the temperatures in the distillation are also affected by setting of a particular concentration. For instance, it is possible to increase the condensation temperature at the top by drawing off not only ammonia but also other components having a higher boiling point than ammonia, for example water, overhead as well. In this case, it is advantageous to operate the condenser in backmixed mode (called "closed condensation" by the person skilled in the art), such that the condensation takes place within a narrow temperature range. A suitable condenser for this type of condensation is one in which the condensation takes place in cocurrent with the outflow of the condensate, or a direct condenser in which cold liquid which is pumped in circulation is brought into contact with the vapors to be condensed.

In a particularly preferred embodiment, in a first stage, the majority of ammonia is distilled off at high pressure, for example higher than 10 bar, preferably higher than bar, more preferably higher than 20 bar, while still permitting a particular ammonia concentration in the bottom, with which the desired bottom temperature is established. The number of separation plates of the column is preferably 2 to 5, more preferably 2 to 4 and especially preferably 2 to 3.

The hydrogen present in the reaction output is generally removed overhead in gaseous form together with ammonia.

The gaseous output from the column is preferably guided through one or more condensers.

Preferably, in a first condenser, the majority of the ammonia is condensed out of the gaseous output (vapors) at a relatively high temperature, preferably at 30 to 80° C., more preferably at 35 to 70° C. and most preferably at 40 to 60° C. Hydrogen is enriched here in the gas phase in accordance with the dew point curve of the mixture. Since complete condensation of the mixture is generally not possible at standard ambient temperatures, this generally gives rise to a gaseous output in the condenser. The latter is preferably introduced into a second condenser in which the temperature can be lowered further by cooling with a colder coolant, such that ammonia is further depleted from the gas phase and a second offgas with lower ammonia content is formed.

The liquid phase that forms in the condensers, comprising ammonia, can be recycled into stage 1) of the process.

The offgas from the first or second condenser can be treated by scrubbing in order to recover the majority of the ammonia present therein. This can be effected by use of standard methods known to those skilled in the art, such as scrubbing columns or Venturi scrubbers. This involves contacting the offgas with a preferably cooled liquid having a higher boiling point than ammonia, preferably water. In a particularly preferred variant, the scrubbing water is taken from another stage in the same process. This affords an ammonia-enriched liquid stream and an ammonia-depleted offgas which generally comprises hydrogen removed. This offgas can be sent to incineration or recycled into an EDA production process. More preferably, the ammonia-enriched stream is recycled into the ammonia removal, preferably to the first stage of the ammonia removal.

Further preferably, the ammonia-containing bottoms output from the first stage of the ammonia removal is guided into a second stage which is operated at a lower pressure than the first stage. The pressure in the second stage is adjusted such that the desired bottom temperature is established, with ammonia being present only in a low concentration, if at all, in the bottoms output from the second stage. The condensation temperature at the top of the second stage is adjusted by entrainment of a component having a higher boiling point than ammonia, preferably water, such that the resulting mixture can be condensed with the desired coolant, for example river water or ambient air. In a particularly preferred variant, the ammonia-comprising mixture drawn off overhead is recycled into the first stage.

It is also possible to subdivide the hydrogen and ammonia removal into a further (zeroth) stage which precedes the first stage and is operated at the same pressure but at a lower bottom temperature than that in the first stage, such that some of the ammonia can be evaporated at a lower temperature. In this way, cheaper energy at lower temperature, for example waste heat, can be used to save on energy costs. Preferably, the vapors from the zeroth stage are condensed in the same condenser as the vapors from the first stage.

In a particularly preferred embodiment, the separation of hydrogen and/or ammonia from the reaction output from stage 1 is effected in that stage 2 comprises the following steps:

2-1) separating the reaction output from stage 1 into a gaseous phase comprising ammonia and/or hydrogen, and a liquid phase comprising ethyleneamines and/or alkanolamines,
2-2) passing the gaseous phase from stage 2-1) through one or more condensers to obtain one or more liquid phases in which ammonia has been enriched, and a gaseous phase in which hydrogen has been enriched,
2-3) contacting the gaseous phase from stage 2-2) with MEG so as to obtain a liquid phase comprising MEG and ammonia and a gaseous phase comprising hydrogen and optionally ammonia.

It has been found that, surprisingly, heat is released in the contacting of the gaseous phase from stage 2-2) comprising hydrogen and ammonia. By virtue of the process of the invention, MEG which is to be guided into stage 1) can be preheated in stages 2-3), which can save energy. In addition, it is found to be advantageous that both the scrubbing liquid and the ammonia are reactants from the process of the invention, and hence can be used together in the process of the invention without further purification.

The reaction output from stage 1 is preferably separated by flashing the reaction output from stage 1) in a stage 2-1).

For this purpose, the reaction output from stage 1) is preferably guided into a flash vessel or separation vessel.

The flash vessel is preferably operated at a pressure in the range from 20 to 80 bar, more preferably 30 to 70 bar and especially preferably 40 to 60 bar.

Flashing to the lower pressure is preferably effected by means of a flash valve and optionally an inlet diffuser or inlet distributor.

The gaseous phase that forms in the flashing is generally drawn off in the upper region of the flash vessel. Preferably, a device for separating out liquid droplets, for example a mesh grid, is mounted upstream of the vapor draw.

The liquid phase that does not evaporate in the flashing is generally collected in the lower region of the vessel and drawn off. The drawing-off can be controlled by means of a closed-loop control valve, such that a constant liquid level can be established in the flash vessel.

The liquid phase generally comprises the components of the reaction output that remain in the liquid phase in the flashing. These are especially the ethyleneamines and/or alkanolamines formed in stage 1), and unconverted MEG. The liquid phase may additionally comprise water.

The gaseous phase that forms in the flashing generally comprises hydrogen and/or ammonia. The temperature of the gaseous phase is generally 50 to 120° C., preferably 60 to 100° C. and more preferably 70 to 90° C.

The gaseous phase from stage 2-1), in the preferred embodiment, is passed through one or more condensers in a stage 2-2). Preferably, the one or more condensers are water-cooled condensers, especially shell and tube condensers or plate heat exchangers.

In the one or more condensers, the temperature of the gaseous phase from stage 1) is lowered.

The lowering of the temperature generally results in enrichment of the hydrogen in the gas phase in accordance with the dew point curve of the mixture introduced into the condenser. Additionally obtained in the condenser is a liquid phase in which ammonia is enriched.

The cooling liquid used for the one or more condensers is preferably water. The cooling water preferably has a temperature of 20 to 90° C., preferably 20 to 50° C. and especially preferably 20 to 30° C.

The one or more condensers are preferably designed such that the temperature of the gaseous phase at the outlet from the one or more condensers is in the range from 25 to 75° C., preferably 30 to 70° C. and especially preferably 40 to 60° C.

In a preferred embodiment, stage 2-2) consists of one condenser.

In a further preferred embodiment, stage 2-2) consists of two condensers.

The gaseous phase from stage 2-2), in a stage 2-3), is contacted with MEG so as to obtain a liquid phase comprising ammonia and MEG, and to obtain a gaseous phase comprising hydrogen and ammonia.

The contacting of the gaseous phase from stage 2-2) with MEG is generally effected in apparatuses suitable for mass transfer. Preferably, the contacting with MEG is effected in a scrubbing column and a Venturi scrubber.

Preferably, the contacting is effected in a scrubbing column.

Preferably, the scrubbing column comprises internals for improving the mass transfer between liquid and gas, especially ordered packings, especially structured packings,
trays, especially bubble-cap trays, centrifugal trays or sieve trays, or
random packings, especially Raschig rings or Pall rings.

The number of theoretical plates is preferably 5 to 40, more preferably 10 to 30 and especially preferably 15 to 25.

The temperature of the MEG which is contacted with the gaseous phase from stage 2-2) in the mass transfer apparatus is preferably at a temperature in the range from to 80° C., more preferably 30 to 70° C. and especially preferably 40 to 60° C. The solubility of ammonia in MEG is sufficiently high within the preferred temperature ranges.

In the mass transfer apparatus, some of the gaseous components of the gaseous phase from stage 2-3) are transferred to the liquid MEG phase. Ammonia is preferably transferred to the liquid MEG phase.

The gaseous phase from stage 2-3) that has not been transferred to the liquid phase (offgas) preferably comprises hydrogen and any ammonia that has not been transferred to the MEG phase.

The gaseous phase from stage 2-3) is preferably recycled into stage 1).

For this purpose, it is generally necessary that the gaseous phase from stage 2-3) is compressed to the pressure that exists in the reactor for stage 1).

The compression is typically effected in a compressor.

It is further preferable to discharge a portion of the gaseous phase from stage 2-3) from the process before the compression. Preferably 10% to 50% by weight, more preferably 15% to 40% by weight and especially preferably 20% to 30% by weight of the gaseous phase from stage 2-3) is discharged from the process.

The discharge of a portion of the gaseous phase has the advantage that the accumulation of by-products, such as methane and CO, can be avoided. The discharge of CO can increase the service life of the amination catalysts in stage 1). The liquid phase from stage 2-3) comprises MEG and ammonia.

It has been found that, surprisingly, the temperature of the MEG increases on contacting with ammonia. Typically, the increase in temperature of the MEG in the mass transfer apparatus is 10 to 100° C., preferably 20 to 80° C., more preferably to 70° C. and especially preferably 40 to 60° C.

Very particular preference is therefore given to introducing the MEG which is to be introduced into stage 1) into stage 2-3) prior to introduction into stage 1). As a result of this, the MEG is preheated, such that less energy has to be applied in order to bring MEG to the reaction temperature that exists in stage 1).

Composition of the Output from the Ammonia Removal

After ammonia and any hydrogen have been separated off, what is preferably obtained is a mixture comprising unconverted MEG, and the reaction products MEA, EDA, PIP, AEEA, AEP, DETA and higher ethyleneamines (higher ethyleneamines refer to ethyleneamines having a boiling point not lower than TETA), for example TETA and TEPA.

The mixture obtained after the removal of ammonia comprises preferably 20% to 75% by weight of EDA, more preferably 30% to 65% by weight of EDA and most preferably 35% to 60% by weight of EDA.

The proportion of ammonia is preferably less than 5% by weight of ammonia, more preferably less than 2% by weight of ammonia, more preferably less than 1% by weight of ammonia and especially preferably less than 0.5% by weight.

The proportion of higher-boiling compounds having a boiling point above the boiling point of EDA, such as the amines MEA, DETA, AEP, AEEA, TETA, TEPA and higher ethyleneamines, and also MEG, is preferably in the range from 5% to 90% by weight, more preferably in the range from 30% to 85% by weight and most preferably in the range from 40% to 70% by weight.

The weight ratio of EDA to Me-EDA is preferably 1:0.0005 (500 ppm by weight of NMEDA) to 1:0.2 (200 000 ppm by weight of NMEDA), more preferably 1:0.001 (1000 ppm by weight) to 1:0.05 (50 000 ppm by weight of NMEDA) and most preferably 1:0.005 (5000 ppm by weight of NMEDA) to 1:0.01 (10 000 ppm by weight of NMEDA).

MEA Removal—Stage a):

According to the invention, a mixture comprising MEG, MEA, EDA and DETA, and low boilers having a boiling point not higher than PIP and high boilers having a boiling point not lower than AEEA is guided into a separation stage in which the mixture introduced is separated into the following mixtures:

(i) a mixture A comprising EDA and the low boilers having a boiling point not higher than PIP; and
(ii) a mixture B comprising MEA; and
(iii) a mixture C comprising MEG, DETA and the high boilers having a boiling point not lower than AEEA.

The separation in stage a) can be conducted in two series-connected rectification columns or in a single rectification column.

2-Stage MEA Removal in Two Rectification Columns

If the separation in stage a) is conducted in two series-connected rectification columns a-1 and a-2, in the first rectification column a-1:

(i) a mixture A comprising EDA and the low boilers having a boiling point not higher than PIP is removed overhead or via a side draw between the feed point and the top, and
(ii) a mixture BC comprising MEA, MEG, DETA and the high boilers having a boiling point not lower than AEEA is drawn off at the bottom or a side draw between the feed point and the bottom.

In the second rectification column a-2:

(i) a mixture B comprising MEA is removed overhead or via a side draw between the feed point and the top, and
(ii) a mixture C comprising MEG, DETA and the high boilers having a boiling point not lower than AEEA is drawn off at the bottom or a side draw between the feed point and the bottom.

Process Parameters for the First Rectification Column a-1

The pressure in the rectification column a-1 is chosen so as to result in suitable bottom and top temperatures. A low pressure facilitates the separation by increasing the relative volatility, as known to those skilled in the art. A low pressure also results in the option of transferring heat at a low temperature in the evaporator and hence using waste heat.

The bottom temperature is generally 100° C. to 250° C., preferably 120° C. to 200° C., more preferably 130° C. to 180° C.

The top temperature is generally 20° C. to 200° C., preferably 40° C. to 150° C., more preferably 50° C. to 90° C.

The number of theoretical plates is generally 20 to 100, preferably 30 to 80, more preferably 35 to 50.

Preferably, the separation is conducted in a single rectification column, wherein the low-boiling fraction is removed overhead or in an upper side draw, the medium-boiling fraction at a side draw between the top and bottom, and the high-boiling fraction at the bottom or a lower side draw.

Internals used may be the customary internals known to those skilled in the art, for example sieve trays or bubble-cap trays. Particular preference is given to the use of structured packings which permit operation at a particularly low pressure drop and high number of stages per meter of height.

Process Parameters for the Second Rectification Column a-2

The pressure in the rectification column a-2 is chosen so as to result in suitable bottom and top temperatures. A low pressure facilitates the separation by increasing the relative volatility, as known to those skilled in the art. A low pressure also results in the option of transferring heat at a low temperature in the evaporator and hence using waste heat.

The bottom temperature is generally 100° C. to 250° C., preferably 120° C. to 200° C., more preferably 130° C. to 180° C.

The top temperature is generally 20° C. to 200° C., preferably 40° C. to 150° C., more preferably 50° C. to 90° C.

The number of theoretical plates is generally 20 to 100, preferably 30 to 80, more preferably 35 to 50.

One-Stage MEA Removal in a Rectification Column

However, preference is given to conducting the removal in stage a) only in a single rectification column a, wherein
(i) a mixture A comprising EDA and the low boilers having a boiling point not higher than PIP is removed overhead or at an upper side draw; and
(ii) a mixture B comprising MEA is removed at a side draw between the top and bottom; and
(iii) a mixture C comprising MEG, DETA and the high boilers having a boiling point not lower than AEEA is drawn off at the bottom or at a lower side draw.

The pressure in the rectification column a is chosen so as to result in suitable bottom and top temperatures. A low pressure facilitates the separation by increasing the relative volatility, as known to those skilled in the art. A low pressure also results in the option of transferring heat at a low temperature in the evaporator and hence using waste heat.

The bottom temperature is generally 100° C. to 250° C., preferably 120° C. to 200° C., more preferably 130° C. to 180° C.

The top temperature is generally 20° C. to 200° C., preferably 40° C. to 150° C., more preferably 50° C. to 90° C.

The number of theoretical plates is generally 20 to 100, preferably 30 to 80, more preferably 35 to 50.

One-Stage MEA Removal in a Dividing Wall Column

In a particularly preferred embodiment, a rectification column a-T with a dividing wall is used.

In a dividing wall column, a vertical dividing wall that divides the cross section into two sections generally runs over part of the height of the column. Above the dividing wall, the liquid phase is collected and distributed between the two column cross sections in a selectable ratio. The use can lead to a reduction in the capital costs and energy demands in the separation.

Preferably, the feed point is on one side of the dividing wall and the position of the middle side draw on the other side of the dividing wall.

Preferably, a mixture A comprising EDA and the low boilers having a boiling point not higher than PIP is removed at the top of the dividing wall column.

Preferably, a mixture B comprising MEA is removed at a side draw of the dividing wall column between the top and the bottom.

Preferably, a mixture C comprising MEG, DETA and the high boilers having a boiling point not lower than AEEA is drawn off at the bottom of the dividing wall column.

The pressure in the dividing wall column a-T is chosen so as to result in suitable bottom and top temperatures. A low pressure facilitates the separation by increasing the relative volatility, as known to those skilled in the art. A low pressure also results in the option of transferring heat at a low temperature in the evaporator and hence using waste heat.

The bottom temperature is generally 100° C. to 250° C., preferably 120° C. to 200° C., more preferably 130° C. to 180° C.

The top temperature is generally 20° C. to 200° C., preferably 40° C. to 150° C., more preferably 50° C. to 90° C.

The number of theoretical plates is generally 20 to 100, preferably 30 to 80, more preferably 35 to 50.

Further Processing of the Mixtures from Stage a)

The mixture A comprising EDA and the low boilers having a boiling point not higher than PIP is generally worked up in two additional process stages. In what is called the NMEDA removal (stage 5), the unwanted NMEDA by-product and water are first removed. Stage 5 can in turn be conducted in two steps, wherein the removal in a first step is effected under conditions under which EDA and water form a high-boiling azeotropic mixture, such that NMEDA can be removed overhead. The second step is preferably conducted under conditions under which water and EDA do not form an azeotrope, such that water can be separated from EDA.

The mixture from the NMEDA removal can be separated into its products of value, EDA and PIP, in a further process stage, called the EDA purification (stage 6).

The NMEDA removal (stage 5) and the EDA purification (stage 6) are described in more detail hereinafter.

Mixture B Comprising Essentially MEA can be Recycled into the MEG Conversion (Stage 1).

Preferably, mixture B comprising essentially MEA is guided into a separate stage 3 (MEA conversion) in which MEA is reacted with ammonia in the presence of hydrogen and an amination catalyst. This embodiment has the advantage that the total amount of AEEA which is formed in the process can be reduced since MEA can react with EDA in the MEG conversion to give AEEA.

The reaction conditions and process parameters described for the MEA conversion correspond generally to the above-described MEG conversion (stage 1).

In general, however, the MEA conversion requires a lower temperature and lower excess of ammonia than in the MEG conversion.

When the MEA conversion is conducted in a separate stage 3, the output from the MEA conversion (stage 3) is preferably combined with the output from the MEG conversion (stage 1) and they are sent together to the ammonia removal (stage 2).

MEG Removal—Stage b):

According to the invention, mixture C comprising MEG, DETA and the high boilers having a boiling point not lower than AEEA is sent to a further separation stage b).

In a preferred embodiment, MEG is additionally introduced into stage b), in the amount as required for the conversion in stage 1. For this purpose, the MEG can be mixed with mixture C prior to introduction into stage b), or the MEG and mixture C can be introduced separately into stage b) and mix in stage b). This embodiment has the advantage that the MEG required in stage 1 can additionally be purified in stage b). Thus, in stage 1, it is possible to use an MEG having a low sulfur content, which can lead to the above-described advantages.

In stage b) mixture C from stage a) is separated into:
(i) a mixture D comprising MEG; and
(ii) a mixture E comprising MEG, DETA and the high boilers having a boiling point not lower than AEEA.

Preferably, the separation is effected in a rectification column b, where mixture D is preferably drawn off as a top product or at an upper side draw and mixture E is preferably drawn off as a bottom product or at a lower side draw.

The pressure at the top of column b is generally 0.1 to 3 bar, preferably 0.2 to 2 bar, more preferably 0.25 to 0.7 bar. The pressure at the top of column b is advantageously chosen such that the heat of condensation obtained in the condenser can be used to operate an evaporator in another part of the process in order to reduce the total energy costs (thermal integration).

The top temperature in rectification column b is generally 30° C. to 220° C., preferably 100° C. to 200° C., more preferably 140° C. to 190° C.

Rectification column b generally comprises 1 to 20 theoretical plates, preferably 2 to 10 theoretical plates and more preferably 3 to 7 theoretical plates.

The separation in rectification column b is effected in apparatuses known to those skilled in the art, such as bubble-cap trays, sieve tray columns or columns having random packings or structured packing. Preference is given to using internals with a low pressure drop, such as structured packings.

Further Processing of the Mixtures from Stage b)

Mixture D from stage b) comprises essentially MEG. Preferably, the MEG thus obtained has a low sulfur content. Preferably, mixture D comprising essentially MEG comprises less than 100 ppm of sulfur in the form of sulfide, sulfite, or an organic sulfur compound such as mercaptans or thiols. More preferably, mixture D comprises less than 20 ppm of sulfur, most preferably less than 2 ppm of sulfur. The introduction of such a low-sulfur MEG into the MEG conversion (stage 1) has the aforementioned advantages.

Mixture E from stage b) comprises MEG, DETA and high boilers having a boiling point not lower than AEEA. The content of DETA and MEG in mixture E corresponds roughly to the composition of the high-boiling DETA/MEG azeotrope.

A particular advantage of stage b) is that the subsequent separation of the high-boiling DETA/MEG azeotrope in stage d) is facilitated since the stream fed in in stage d) generally comprises only the amount of MEG as corresponds to the composition of the DETA/MEG azeotrope. The stream which is introduced into stage d) thus generally comprises only a small degree, if any, of excess MEG. The lower flow rate which is introduced into stage d) reduces the energy demands and apparatus sizes. In addition, the thermal stress on the products in step d) can be reduced, which leads to a higher quality of the products.

AEEA/Residue Removal—Stage c):

According to the invention, the mixture E from stage b) comprising MEG, DETA and high boilers having a boiling point not lower than AEEA is separated in a stage c):
(i) into a mixture F comprising MEG and DETA; and
(ii) into a mixture G comprising the high boilers having a boiling point not lower than AEEA.

Alternatively, the separation of mixture E from stage b can be separated as follows:
(i) a mixture F comprising MEG and DETA; and
(ii) a mixture G1 comprising AEEA; and
(iii) a mixture G2 comprising the high boilers having a boiling point not lower than AEEA.

The separation in stage c) is preferably effected in a rectification column c.

In the rectification column c, mixture F is preferably drawn off overhead or via an upper side draw and mixture G is preferably drawn off via the bottom or a lower side draw.

It is also possible to draw off a mixture F overhead and a mixture G1 via a middle side draw and a mixture G2 via the bottom or a lower side draw.

The rectification in stage c is generally conducted in rectification setups known to those skilled in the art, such as bubble-cap tray columns, sieve tray columns or columns having random packings or structured packings.

Preference is given to using structured packings having a low pressure drop.

If mixture E is separated into three fractions F, G1 and G2, the rectification column c used is preferably a dividing wall column.

The number of theoretical plates is 5 to 50, preferably 10 to 30, more preferably 15 to 20.

The pressure at the top of the column is 0.01 to 3.0 bar, preferably 0.05 to 1 bar, more preferably 0.1 to 0.5 bar.

The top temperature in rectification column b is generally 30° C. to 220° C., preferably 100° C. to 200° C., more preferably 120° C. to 180° C.

Further Processing of the Mixtures from Stage c)

Mixture G comprising the high boilers having a boiling point not lower than AEEA is generally worked up in a further separation stage, for example a rectification, a distillation or a simple evaporation in a circulation evaporator, falling-film evaporator or thin-film evaporator, in order to separate AEEA from high boilers having a boiling point greater than AEEA.

Mixture G1 comprising essentially AEEA can also be sent directly to a further use. For example, AEEA can be used as a synthesis chemical for preparation of other chemical compounds such as fuel additives and oil additives, chelate ligands, surfactants, coatings, fabric softeners, urethanes inter alia. It is also possible to further purify AEEA when a particularly high quality is required.

Mixture G2 comprising high boilers having a boiling point greater than AEEA can likewise be sent to a use, for example as asphalt additive, corrosion inhibitor, fuel additive and oil additive, surfactants or as hardener for epoxy systems.

DETA Removal—Stage d):

According to the invention, mixture F from stage c) is separated by extractive distillation with triethylene glycol (TEG) into:
(i) a mixture H comprising MEG; and
(ii) a mixture I comprising DETA and TEG.

Before mixture F is introduced into stage d), TEG is fed into mixture F.

The extractive distillation with TEG as selective solvent for DETA is preferably operated in such a way that the molar ratio of TEG to DETA in mixture F after TEG has been fed in is in the range from 1:1 to 10:1, more preferably 2:1 to 8:1 and most preferably 3:1 to 5:1.

The extractive distillation in stage d) is preferably conducted in a rectification column d.

Preferably, mixture H is drawn off at the top or in an upper side draw, while mixture I is drawn off as bottom product or from a lower side draw.

The rectification in stage d) is preferably conducted in rectification setups known to those skilled in the art, such as bubble-cap tray columns, sieve tray columns or columns having random packings or structured packings. Preference is given to using structured packings having a low pressure drop.

The number of theoretical plates is generally 10 to 100, preferably 20 to 60, more preferably 30 to 50.

The pressure at the top of the column is generally 0.005 to 1.0 bar, preferably 0.01 to 0.2 bar, more preferably 0.02 to 0.1 bar.

The top temperature in rectification column d is generally 50° C. to 220° C., preferably 70° C. to 160° C., more preferably 80° C. to 130° C.

Further Processing of the Mixtures from Stage d)

Mixture H comprising essentially MEG is preferably recycled into the MEG conversion.

The process of the invention can optionally be combined with further stages to give a particularly advantageous overall process.

Thus, preference is given to introducing mixture I comprising DETA and TEG which is obtained in stage d) into a further stage 4 (TEG removal) in which it is separated into:
(i) a mixture J comprising DETA; and
(ii) a mixture K comprising TEG.

Mixture A from stage a) is preferably introduced into a stage 5 (EDA dewatering) in which it is separated into:
(i) a mixture L comprising NMEDA and water; and
(ii) a mixture M comprising water; and
(iii) a mixture N comprising EDA and PIP.

Mixture N from stage 5 is preferably separated in a further stage 6 (EDA purification) into the following mixtures:
(i) a mixture O comprising EDA; and
(ii) a mixture P comprising PIP; and
(iii) a mixture Q comprising a residue.

Optional Stages:

TEG Removal—Stage 4

Preference is given to introducing mixture I comprising DETA and TEG which is obtained in stage d) into a further stage 4 in which it is separated into:
(i) a mixture J comprising DETA; and
(ii) a mixture K comprising TEG.

Stage 4 is preferably conducted in a rectification column in which mixture J is drawn off overhead or from an upper side draw and mixture K is drawn off as the bottom product or from a lower side draw.

The rectification in stage 4 is preferably conducted in rectification setups known to those skilled in the art, such as bubble-cap tray columns, sieve tray columns or columns having random packings or structured packings. Preference is given to using structured packings having a low pressure drop.

The number of theoretical plates in column e is generally 5 to 60, preferably 10 to 50, more preferably 20 to 40.

The pressure at the top of column e is generally 0.005 to 1.0 bar, preferably 0.01 to 0.2 bar, more preferably 0.02 to 0.1 bar.

The top temperature in rectification column e is generally 50° C. to 220° C., preferably 70° C. to 160° C., more preferably 80° C. to 130° C.

Further Processing of the Mixtures from Stage 4

Mixture J comprising essentially DETA can be sent to a further use, for example as chelate ligand, as hardener for epoxy systems and as intermediate for production of crop protection compositions and pharmaceuticals.

Mixture K comprising essentially TEG is preferably, as detailed above, mixed with mixture F from stage c) prior to introduction into stage d).

EDA Dewatering—Stage 5

Mixture A from stage a) is preferably introduced into a stage 5 (FDA dewatering) in which it is separated into:
(iv) a mixture L comprising NMEDA and water; and
(v) a mixture M comprising water; and
(vi) a mixture N comprising EDA and PIP.

The separation is preferably conducted in a sequence of two rectification columns 5-1 and 5-2.

NMEDA Removal Column 5-1

In rectification column 5-1, mixture L is preferably removed overhead, and a mixture MN comprising the essential proportion of EDA as a high-boiling azeotrope with water and piperazine via the bottom.

The bottom temperature in 5-1 is preferably less than 170° C., more preferably less than 160° C., most preferably less than 155° C.

The rectification temperature is generally attained via establishment of a suitable pressure in the rectification.

Preference is given to conducting the distillation under conditions under which water and EDA form a high-boiling azeotrope. For this purpose, additional water as required for the formation of a high-boiling azeotrope is optionally supplied to the mixture. In the presence of other substances that form a high-boiling azeotrope with water, it is additionally necessary for at least the amount of water that corresponds to the respective concentration of the respective component that forms a high-boiling azeotrope with water to be present.

The determination of the azeotropic compositions is familiar to the person skilled in the art. For further details reference is made to EP 2 507 202.

Preference is given to choosing a minimum pressure for the rectification, more preferably one at which condensation of the vapor mixture obtained at the top under industrially customary conditions, i.e. a temperature at which condensation with cooling water or by cooling with ambient air is still possible. These are typically top temperatures of 20° C. or more, preferably 30° C. or more and more preferably 35° C. or more. The condensation is preferably effected within a temperature range from 20 to 60° C., preferably 30 to 55° C., more preferably 40 to 50° C.

Preferably, a pressure at the top of the column of 2.5 bar or less, preferably 1.6 bar or less and more preferably 1 bar or less is established.

If the input into the rectification column comprises higher-boiling amines, it is generally necessary to lower the top pressure in order to attain the temperature according to the invention in the bottom of the column.

The rectification can be effected in apparatuses known to those skilled in the art, such as bubble-cap tray columns, sieve tray columns or columns having random packings or structured packings. Preference is given to using internals with a low pressure drop, such as structured packings, for example in the form of sheet metal packing such as Mellapak 250 Y or Montz Pak (B1-250 type). It is also possible for a packing with lower or elevated specific surface area to be present, or it is possible to use a fabric packing or a packing with another geometry such as Mellapak 252.Y. What are advantageous about the use of these distillative internals are the low pressure drop and low specific liquid holdup compared to valve trays, for example. The internals may be disposed in one or more beds.

The rectification column preferably comprises 35 to 140 theoretical plates, more preferably 50 to 120 theoretical plates and most preferably 60 to 100 theoretical plates.

The input into the rectification column is preferably fed in in a spatial region between 25% and 95% of the theoretical plates of the rectification column (counted from the bottom), more preferably in a spatial region between 60% and 90% of the theoretical plates of the rectification column. For example, the feeding can be effected above the middle of the theoretical plates.

To improve the removal of NMEDA, the condensate obtained in the condenser is preferably recycled into the top of the rectification column to an extent of more than 30%, preferably to an extent of more than 50%. The remainder is discharged from the process and generally sent to a collecting vessel and thence generally to a disposal, preferably a water treatment plant.

Mixture L comprising essentially water and NMEDA and possibly traces of EDA is preferably withdrawn in the upper region of the column, more preferably at the top of the column, and sent to a condenser. Condensers used may, for example, be condensers having cooling coils or helical tubes, jacketed tube condensers and shell and tube heat exchangers.

To improve the removal of NMEDA, the condensate obtained in the condenser is preferably recycled into the top of the rectification column to an extent of more than 30%, preferably to an extent of more than 50%. The remainder is discharged from the process and generally sent to a collecting vessel and thence generally to a disposal, preferably a water treatment plant.

In the lower region of the column, preferably from the bottom or a lower side draw, a mixture MN comprising the essential proportion of EDA as a high-boiling azeotrope with water and piperazine is drawn off.

EDA Dewatering Column 5-2

The mixture MN is preferably guided into a further rectification column 5-2 in which the mixture M is drawn off preferably overhead or via an upper side draw, and mixture N is drawn off at the bottom or a lower side draw.

Preferably, the EDA dewatering column 5-2 is operated under conditions under which EDA and water form an azeotropic mixture.

The pressure in column 5-2 is generally set such that the bottom temperature is higher than 180° C., preferably higher than 190° C., more preferably higher than 200° C.

In the preferred embodiment, therefore, the absolute pressure at the top of the rectification column is preferably in the range from 4 to 30 bar, more preferably 6 to bar and especially preferably 7 to 9 bar.

The feed is more preferably in a spatial region between 50% and 100% of the theoretical plates of the rectification column. For example, the feed may be to the top of the column. The optimal feed point can be ascertained by the person skilled in the art with the customary calculation tools.

The number of theoretical plates is generally in the range from 10 to 80, preferably to 60.

In a preferred embodiment, the EDA dewatering column has a condenser which is generally operated at a temperature at which the predominant portion of the water is condensed at the corresponding top pressure.

In general, the operating temperature of the condenser is in the range from 150 to 230° C., preferably 160 to 195° C.

A condensate comprising predominantly water is generally obtained in the condenser.

Preferably, the condensate obtained in the condenser is recycled into the top of rectification column to an extent of more than 50%, preferably to an extent of more than 65%.

The unrecycled condensate can generally be sent directly to disposal, for example by introduction into a wastewater treatment plant.

In a further preferred embodiment, the condensate not recycled into the EDA dewatering is introduced into the bottom of the NMEDA removal column 5-1. This has the advantage that the amount of water in the NMEDA removal column is increased, and so the NMEDA removal column comprises as much water as required for the formation of a high-boiling azeotrope of EDA and water.

In a preferred embodiment, the mixture M comprising essentially water which is drawn off at the top of the EDA dewatering column 5-2 is not condensed and is introduced into the NM EDA removal column 5-1 in the form of vapors ("vapors" are understood here to mean the generally vaporous stream obtained at the top of a column before it is sent to a condenser).

The vapors can be introduced directly into the stripping section of column 5-1, preferably the bottom. It is advantageous here to throttle the vapor stream from 5-2 to 5-1 to the lower pressure with the aid of a closed-loop control valve or closed-loop control flap, or to undertake the throttling using a turbine that drives a motor that generates flow.

The vapors can be passed into an evaporator of column 5-1 in the form of heating vapor.

In both cases, the energy required in the evaporator of column 5-1 is reduced by a considerable magnitude.

EDA Purification—Stage 6

Mixture N from stage 5 comprising EDA and PIP is preferably separated in a further stage 5 as follows:
(iii) a mixture O comprising EDA; and
(iv) a mixture P comprising PIP; and
(v) a mixture Q comprising a residue.

The separation in stage 6 is preferably conducted in a rectification column 6-1.

Preference is given here to drawing off a mixture O comprising essentially EDA overhead or via an upper side draw above the feed.

Preferably, a mixture P comprising essentially PIP is drawn off in the side draw or via the bottom.

A mixture Q generally comprising high boilers having a higher boiling point than PIP can optionally be drawn off as residue from the bottom.

The separation is effected in columns known to those skilled in the art, such as bubble-cap tray columns, sieve tray columns or columns having random packings or structured packings.

The rectification column comprises 10 to 70 theoretical plates, preferably 20 to 60 theoretical plates and more preferably 30 to 50 theoretical plates.

The pressure at the top of the column is 0.1 to 10 bar, preferably 0.5 to 5 bar, more preferably 1.0 to 3 bar.

It is possible to choose the pressure in the column and hence the top temperature at the condenser in such a way that the heat of condensation obtained can be used for heating of a further evaporator in the process, in order to save on energy costs.

Advantages

The process of the invention for separation of a mixture which is preferably obtainable from the conversion of MEG has provided a process which enables the desired process products to be obtained in high yield and purity.

In addition, it is possible in the process of the invention to recycle unconverted or partly converted products into the process, such that a high overall yield based on the reactants used can be achieved.

Moreover, the process has a lower energy demand and requires smaller apparatuses in the comparatively complex extractive distillation owing to smaller flow rates. As a result, it is also possible to reduce thermal stress in the extractive distillation, which can lead to an improvement in product quality.

The process of the invention additionally enables a special prepurification of the MEG reactant used, in which reduction in the proportion of sulfur compounds in the MEG is enabled. This can in turn have an effect on the conversion and yield in the MEG conversion and improve the service life of the amination catalysts used in the MEG conversion.

The process of the invention additionally enables integration with other process steps.

For instance, the product stream B obtained in stage a) of the process of the invention can be converted in a separate MEA conversion (stage 3) to the EDA and DETA target products. Thus, in the overall process, it is possible to increase the selectivity for EDA and DETA, while the selectivity for AEEA can be reduced.

In addition, it is possible to couple stage d) with an efficient TEG removal (stage 4), such that TEG can be recycled back into the process (stage d). The combination of stage b) can reduce the flow rate introduced into stage 4, which can in turn lead to a reduction in the apparatus size and the energy demand.

The coupling of stage a) with an NMEDA removal (stage 5) and an EDA purification (stage 6) enables purification of the mixture A removed in stage a) in such a way that on-spec EDA having a low NMEDA content can be prepared. Stage 5 can in turn be executed in an advantageous embodiment in such a way that the energy demand in stage 5 can be reduced by an interconnection of the columns used in stage 5.

The process of the invention is elucidated by examples which follow.

EXAMPLE 1

Figure 2:
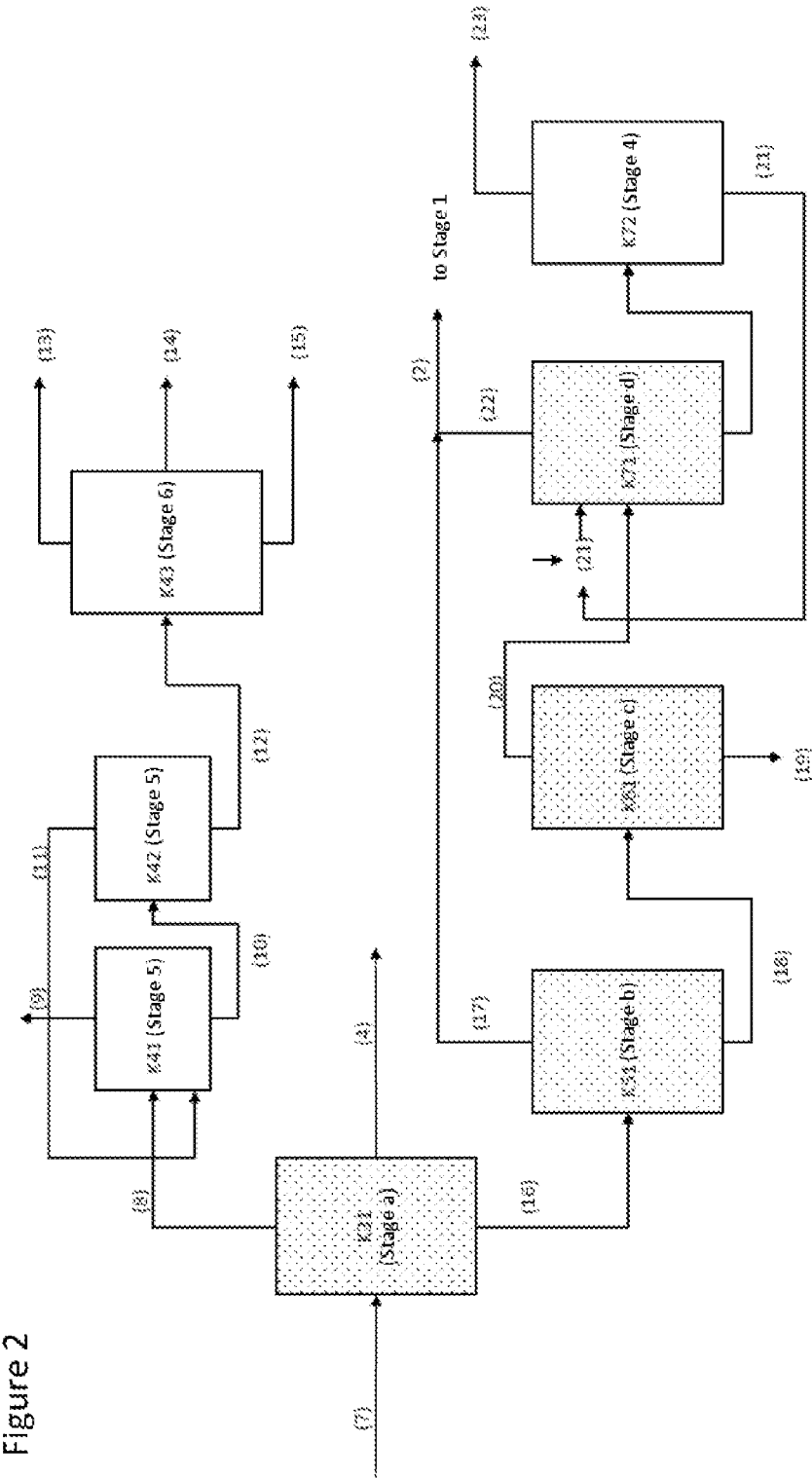
FIG. 2 illustrates example 1, was conducted according to the arrangement shown in the figure.

Example 1 was conducted according to the arrangement shown in FIG. 1 and FIG. 2.

The mixture comprising MEG, MEA, EDA and DETA was prepared in two parallel stages (stage 1: MEG conversion and stage 3: MEA conversion), as shown in FIG. 1.

In stage 1, a stream (1) comprising 53.5 kg/h of ammonia in liquid form at 190 bar is mixed with a stream (2) consisting of 13.9 kg/h of MEG at 190 bar, and a further stream (1-1) consisting of 350 g/h of hydrogen, heated to 175° C. and through a tubular reactor (R1) comprising 20 kg of an Ni-, Co-, Cu-, Ru- and Sn-containing catalyst.

The catalyst was prepared as follows: A catalyst precursor was prepared according to example B3 of WO 2013/072289. The tablets thus obtained (3*3 mm) were comminuted to 1-2 mm spall. The maximum water absorption capacity of the spall was 0.30 mL/g. A metal salt solution was prepared. For this purpose, 20.25 g of cobalt nitrate hexahydrate (20.25% by weight of Co) were dissolved in hot water, and 37.91 g of ruthenium nitrosylnitrate solution were added. The solution thus obtained was made up to 71 mL with demineralized water and transferred to a spray vessel. The spall was sprayed in an impregnation apparatus with an amount that corresponds to 95% of the maximum water absorption of the spall. In order to ensure homogeneous uptake of the impregnation solution, the spall was rotated for a further 30 min. Thereafter, the catalyst spall was dried in an air circulation drying cabinet at 120° C. for 16 h. After the drying, the catalyst precursor was reductively calcined at not more than 200° C. in a stream of nitrogen and hydrogen.

In stage 3, a stream (3) comprising 4.7 kg/h of ammonia in liquid form at 190 bar was mixed with a stream (4) consisting of 1.88 kg/h of MEOA at 190 bar and a further stream (3-1) consisting of 65 g/h of hydrogen at 190 bar, heated to 150° C. and passed through a reactor (R2) comprising 5 kg of catalyst (for preparation see above).

The reaction outputs from stage 1 and stage 3 were combined and guided into the ammonia removal (stage 2).

Stage 2 was conducted in two steps in two rectification columns (K21 and K22).

In a first step, the combined mixtures from stages 1 and 3 were guided into a rectification column (K21) having solely a stripping section with 2 theoretical plates. K21 was operated at a top pressure of 20 bar and a bottom temperature of 165° C. A temperature of 49° C. was measured at the top of K21. The ammonia present was removed overhead in K21 and recycled as streams (1) and (3) into stages 1 and 3, with addition of a small stream of fresh ammonia to compensate for losses. A small amount of offgas additionally arose at the condenser of K21, consisting mainly of the amount of hydrogen present in the ammonia feeds, streams (1) and (3). The bottoms output from column K21, stream (5), was introduced into a further column (K22) that comprised solely a stripping section with 5 theoretical plates. K21 was operated at a top pressure of 4 bar and a bottom temperature of 173° C. At the top of K21, a mixture of ammonia and water at 55° C. was drawn off as stream (6) and recycled into column K21. The ammonia-free bottoms output from column K22 was introduced into the process of the invention as stream (7).

Stage a)

The output from stage 2 (stream (7)) was guided into stage a) as shown in FIG. 2. Stage a) is configured as a dividing wall column that was operated at a top pressure of 150 mbar. Column K31 comprised an ordered packing corresponding to 16 theoretical plates as stripping section below the dividing plate, 5 theoretical plates on the feed side of the dividing plate below the feed point, 10 theoretical plates on the feed side of the dividing plate above the feed point, 12 theoretical plates on the draw side of the dividing plate below the side draw point, 8 theoretical plates on the draw side of the dividing plate above the side draw point, and 3 theoretical plates as rectifying section above the dividing plate. The top temperature in K31 was 73° C., the bottom temperature 146° C., and the reflux rate 10.6 kg/h. At the side draw of K31, a stream comprising 1.88 kg/h of MEA was drawn off (mixture B), which was guided as stream (4) into stage 3.

Stage 5) NMEDA Removal

At the top of column K31, a stream (8) comprising EDA and low boilers having a boiling point not higher than PIP (mixture A) was drawn off, which was guided into the NMEDA removal (stage 5), as shown in FIG. 2.

Stage 5 was conducted in two steps in two rectification columns.

The first rectification column K41 was operated at a top pressure of 150 mbar. Column K41 comprised an ordered packing corresponding to 13 theoretical plates in the rectifying section and 67 theoretical plates in the stripping section. The top temperature was 55° C., the bottom temperature 79° C., and the reflux rate 5 kg/h. 3.3 kg/h of water were drawn off overhead as stream (9), which comprised 100 ppm of EDA and 1217 ppm of NMEDA (mixture L). A stream (10) at 12 kg/h, comprising 1 ppm of NMEDA, was drawn off via the bottom of K41. Stream (10) was guided into a second rectification column K42 that consisted of a stripping section with ordered packing corresponding to 60 theoretical plates. The top pressure was 8.5 bar, the top temperature 189° C. and the bottom temperature 204° C. K42 did not comprise any condenser; all the vapors from the column were introduced as stream (11) into the bottom of K41. A stream (6) comprising water (mixture M) was drawn off overhead in K42. 4.6 kg/h were drawn off via the bottom of K42 as stream (12) comprising EDA, PIP and 0.35% water, and passed into the EDA removal (stage 6).

Stage 6) EDA Removal

Stage 6 was conducted in one step in one rectification column as shown in FIG. 2. The mixture from stage 5 was introduced into a rectification column K43 that was operated at a top pressure of 1050 mbar and comprised a lower side draw in vaporous form, but no dividing plate. Column K43 comprised ordered packing corresponding to 25 theoretical plates in the rectifying section, 15 theoretical plates in the stripping section between feed and side draw, and 5 theoretical plates between side draw and bottom. The top temperature was 118° C., the bottom temperature 149° C., and the reflux rate 8.6 kg/h. 4.1 kg/h of EDA having a content of 0.4% water and 100 ppm of piperazine were drawn off overhead as stream (13) as pure product (mixture O). At the side draw, 0.48 kg/h of piperazine with a content of 98 ppm of EDA was drawn off as stream (14) (mixture P). 50 g/h of residue were drawn off via the bottom as stream (15) (mixture Q).

Stage b)

At the bottom of column K31, 8.7 kg/h which comprise MEG, DETA and the high boilers having a boiling point not lower than AEEA were drawn off as stream (16) (mixture C). This stream was guided into stage b) to a rectification column K51, as shown in FIG. 2. Column K51 was operated at a top pressure of 300 mbar. Column K51 comprised only a stripping section with an ordered packing corresponding to 6 theoretical plates. The top temperature was 161° C., the bottom temperature 179° C. 7.8 kg/h of MEG comprising 0.4% DETA and 0.5% AEEA, and also 0.6% of other high boilers were drawn overhead as stream (17) (mixture D). 0.91 kg/h comprising 34% MEG, 34% DETA, 16% AEEA, the balance being (16%) other high boilers, was drawn via the bottom of K51 as stream (18) (mixture E).

Stage c)

The bottom product from stage b) was guided in a stage c) into a rectification column K61, as shown in FIG. 2. Column K61 was operated at a top pressure of 125 mbar. Column K61 comprised an ordered packing corresponding to 15 theoretical plates in the rectifying section and 12 theoretical plates in the stripping section. The top temperature was 150° C., the bottom temperature 180° C., the reflux rate 0.8 kg/h. 0.29 kg/h of residue comprising AEEA was drawn off via the bottom as stream (19) (mixture G). 0.62 kg/h comprising about 50% MEG and 50% DETA with 110 ppm of other high boilers was drawn overhead as stream (20) (mixture F).

Stage d)

Stream (20) was guided in a stage d) into a rectification column K71, as shown in FIG. 2. Column K71 was operated at a top pressure of 30 mbar. In addition, 4 kg/h comprising mainly TEG were guided into K71 as stream (21). K71 comprised ordered packing corresponding to 6 theoretical plates as rectifying section above the feed of stream (21), 14 theoretical plates between the feeds of stream (21) (top) and stream (20) (bottom), and 23 theoretical plates as stripping section below the feed point of stream (20). The top temperature was 109° C., the bottom temperature 188° C., and the reflux rate 0.93 kg/h. 0.31 kg/h of MEG comprising 950 ppm of DETA was drawn off overhead in K71 as stream (22) (mixture H). Stream (22) from the top of K71, stream (17) from the top of K51 and fresh MEG to supplement the amount consumed were combined and recycled as stream (2) into stage 1.

4.3 kg/h comprising DETA and TEG were drawn off via the bottom of K71 as stream (23) (mixture I).

Stage 4) TEG Removal

The bottoms from K71 were introduced in a stage 4 into a rectification column K72, as shown in FIG. 2. Column K72 was operated at a top pressure of 25 mbar. Column K72 comprised ordered packing corresponding to 6 theoretical plates in the rectifying section and 24 theoretical plates in the stripping section. The top temperature was 105° C., the bottom temperature 190° C., the reflux rate 1.4 kg/h. In K72, 0.31 kg/h of DETA comprising 101 ppm of MEG and 2500 ppm of other high boilers was drawn off as stream (23) as product (mixture J)). At the bottom of K72, 4 kg/h comprising TEG were drawn off (mixture K), which were recycled as stream (21) into column K71 in stage d). Also discharged from the bottom of K72 were 10 g/h in order to avoid accumulation of inert high boilers in the TEG circuit.

EXAMPLE 2

Figure 3:
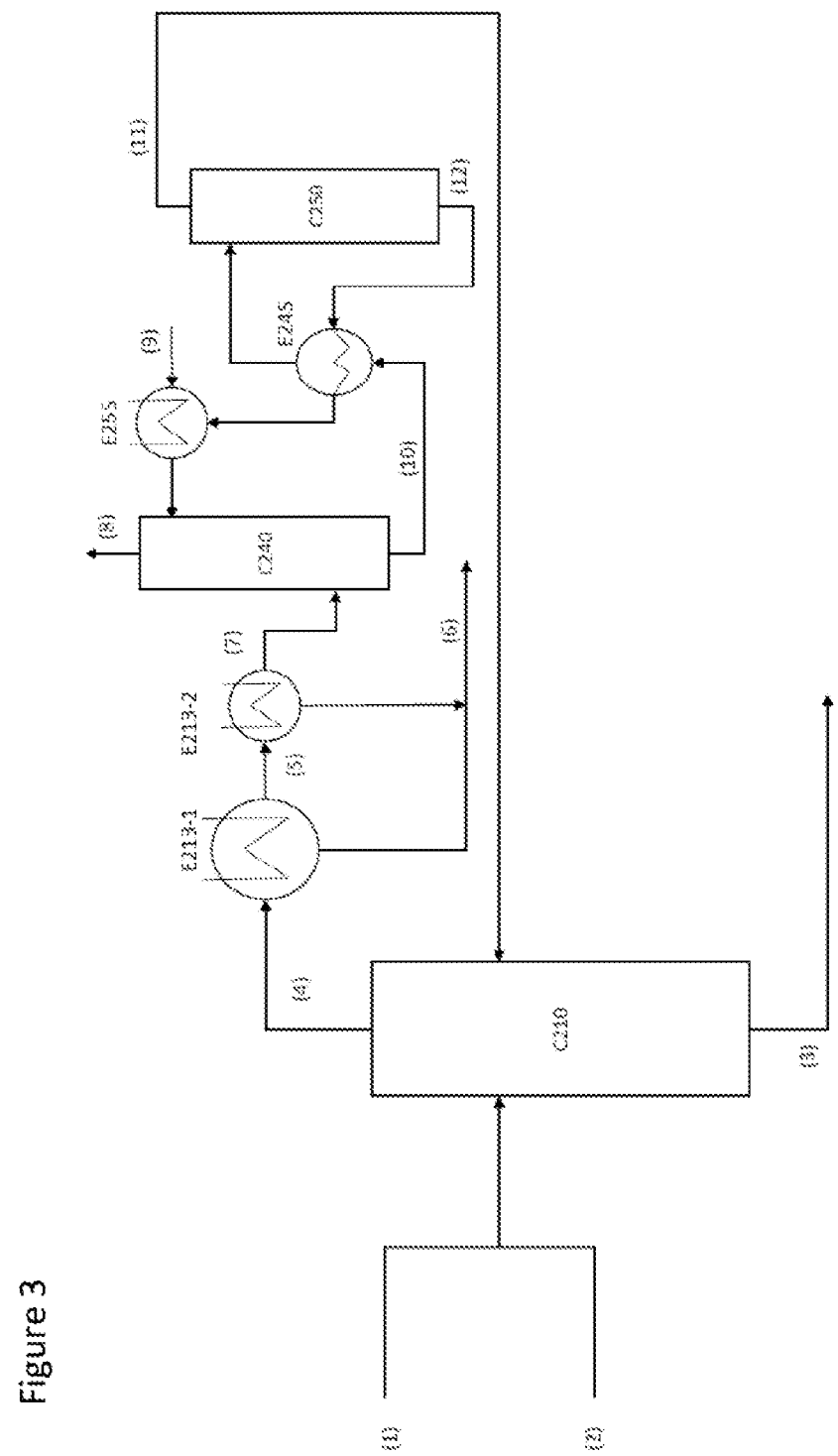
FIG. 3 illustrates example 2, the removal of ammonia (stage 2) is conducted in multiple columns, as shown in the figure.

In example 2, the removal of ammonia (stage 2) is conducted in multiple columns, as shown in FIG. 3.

The output from stage 1 (stream (1)) and stage 3 (stream (2)) is guided collectively into a column C210 which is operated at 20 bar.

The number of theoretical plates is 2. At a top temperature of about 50° C., a gaseous stream (stream (4)) comprising hydrogen and ammonia is fed to a first condenser in which the gaseous mixture is cooled down from 50° C. to 45° C. The gaseous mixture from the first condenser (E213-1) is guided into a second condenser (E213-2) (stream (5)) in which the gaseous mixture is cooled down to 35° C. The liquid phases consisting predominantly of ammonia are combined and recycled into stage 1) as stream (6).

The bottom product from column C210 is guided into a further column C220 which has 2 theoretical plates and is operated at a pressure of 20 bar. At the top of column C220, at a top temperature of about 49° C., a stream comprising predominantly ammonia is drawn off, which is preferably recycled into stage 1 and/or stage 3. The bottom product from column C220 is introduced into a further column C230, which is operated at 4 bar and has 5 theoretical plates. At the top of column C230, at a top temperature of about 55° C., a mixture comprising predominantly ammonia and methylamine is drawn off. The bottom product is guided into stage a).

The gaseous phase (stream (7)) from the condenser E213-2 is guided into a scrubbing column C240 in which the gaseous phase is contacted with water (stream (9)) in countercurrent. The scrubbing water has a temperature of 35° C. The scrubbing water (stream (9)) is preferably water which has been used as cooling water in other parts of the process, for example for cooling the condenser in the EDA removal (stage 6). At the top of column C240, a gaseous phase is drawn off (stream (8)), which consists predominantly of hydrogen. The scrubbing water (stream (10)) enriched with ammonia is guided from the bottom of column C240 through a heat exchanger E245, where it is heated to about 140° C., and guided onward into a column C250 (stream (9)). Column C250 is operated at a pressure of bar and a bottom temperature of 217° C. At the top of column C250, ammonia is drawn off (stream (11)), which is condensed and recycled into column C210. The scrubbing water that has been very substantially freed of ammonia is recycled into column C240 via heat exchangers E245 and E255 (stream (11)). In the heat exchanger, some of the thermal energy in stream (12) is used to heat up stream (10) from column C240.

EXAMPLE 3

Figure 4:
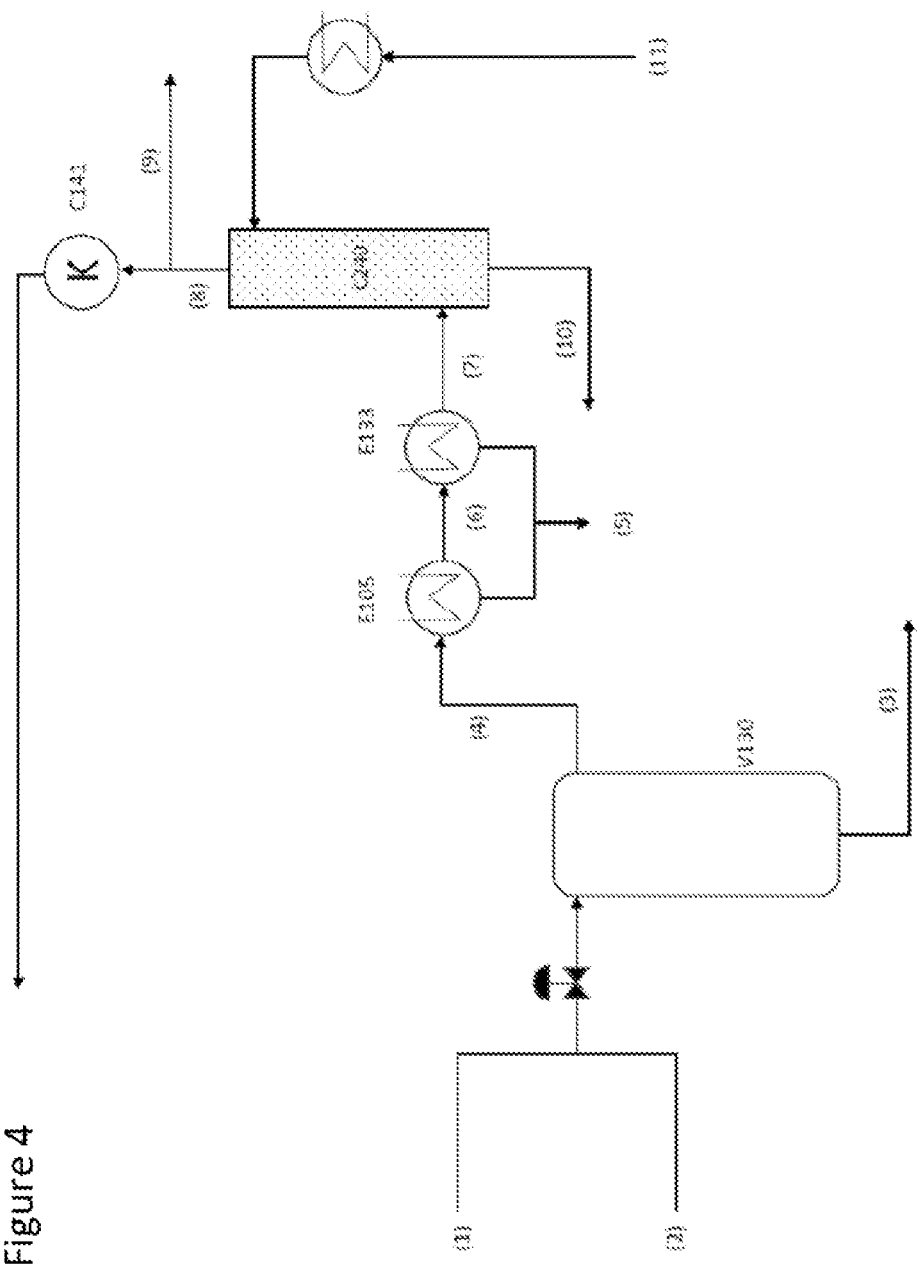
FIG. 4 illustrates example 3, the removal of ammonia is conducted in multiple columns, as shown in the figure.

In example 3, the removal of ammonia is conducted in multiple columns, as shown in FIG. 4.

The output from stage 1 (stream (1)) and stage 3 (stream (2)) is combined and guided into a flash vessel (V130) via a flash valve. The flash vessel is at a pressure of 50 bar. The gaseous phase that forms in the flashing (stream (4)), comprising hydrogen and ammonia, is guided through a first condenser (E105), wherein the temperature of the gas phase is lowered from 81° C. to 72° C. The condensate that forms in the cooling (stream (5)), which consists predominantly of ammonia, is drawn off and preferably recycled into stage 1 or 3. The gaseous phase from condenser E105 is guided through a second condenser E133 (stream (6)), in which the temperature of the gas stream is lowered from 72° C. to 50° C. The condensates that form (stream (5)) are combined with the liquid condensates from condenser E105 and, as described above, recycled preferably into stage 1 and/or stage 3. The gaseous phase from condenser E133 (stream (7)) is contacted with MEG in scrubbing column C240. In scrubbing column C240, MEG is laden with ammonia. The ammonia-laden MEG (stream (10)) is recycled into stage 1 and/or stage 3. In the scrubbing column, the MEG is heated from about 46° C. to 91° C. The scrubbing liquid used is preferably MEG which, before being introduced into stage 1, is introduced into the scrubbing column C240 (stream (11)), such that the MEG is preheated before being introduced into stage 1 (stream (10)). The unabsorbed gas phase from the scrubbing column C240, comprising predominantly hydrogen (stream (8)), is compressed in a compressor C141 to the reaction pressure that exists in stage 1 and recycled into stage 1. It is preferable to withdraw a small stream (9) in order to avoid the accumulation of CO and methane in the recycled hydrogen.

The liquid phase from flash vessel V130 is transferred into a multistage distillation in which, at 50 bar, ammonia is first removed overhead and the bottom product is guided into a second column in which, at 4 bar, further ammonia and methylamine are removed overhead. The bottom product from the second distillation column is guided into stage a) (MEA removal).

The process variant detailed in example 3 has the advantage over the process variant from example 2 that the scrubbing liquid used is a reactant which can be used in the MEG conversion (stage 1) without further purification. The scrubbing water from example 2, by contrast, has to be worked up in further process steps. It has further been found that, surprisingly, the MEG scrubbing liquid is heated on contacting with ammonia in column C240. Thus, MEG can already be heated before being introduced into the MEG conversion (stage 1), such that less energy is required to heat the products in stage 1.

The invention claimed is:

1. A process for purifying a mixture comprising MEG, MEA, EDA and DETA, and low boilers having a boiling point not higher than PIP and high boilers having a boiling point not lower than AEEA, wherein the process comprises the following steps:
   a) separating a mixture comprising MEG, MEA, EDA and DETA, and low boilers having a boiling point not higher than PIP and high boilers having a boiling point not lower than AEEA, into
      (i) a mixture A comprising EDA and the low boilers having a boiling point not higher than PIP; and
      (ii) a mixture B comprising MEA; and
      (iii) a mixture C comprising MEG, DETA and the high boilers having a boiling point not lower than AEEA;
   b) separating mixture C from stage a) into
      (i) a mixture D comprising MEG; and
      (ii) a mixture E comprising MEG, DETA and the high boilers having a boiling point not lower than AEEA;
   c) separating mixture E from stage b) either into
      (i) a mixture F comprising MEG and DETA; and
      (ii) a mixture G comprising the high boilers having a boiling point not lower than AEEA;
      or into
      (i) a mixture F comprising MEG and DETA; and
      (ii) a mixture G1 comprising AEEA; and
      (iii) a mixture G2 comprising the high boilers having a boiling point higher than AEEA;
   d) separating mixture F from stage c) by extractive distillation with triethylene glycol (TEG) into
      (i) a mixture H comprising MEG; and
      (ii) a mixture I comprising DETA and TEG.

2. The process according to claim 1, wherein mixture introduced into the process is prepared in a stage 1 in which MEG is reacted with ammonia in the presence of hydrogen and an amination catalyst, and the reaction product from stage 1 is guided into a stage 2 in which ammonia and hydrogen are separated off.

3. The process according to claim 2, wherein mixture B is recycled from stage a) into stage 1 or is reacted in an additional stage 3 (MEA conversion) with ammonia in the presence of hydrogen and an amination catalyst and the reaction product thus obtained from stage 3 is combined with the reaction product from stage 1 before the combined stream is introduced into stage 2.

4. The process according to claim 1, wherein mixture A from stage a) is separated in a stage 5 (NMEDA removal) into:
   (vii) a mixture L comprising NMEDA and water; and
   (viii) a mixture M comprising water; and
   (ix) a mixture N comprising EDA and PIP.

5. The process according to claim 4, wherein the separation in stage 5 is effected in two rectification columns 5-1 and 5-2, where, in column 5-1, mixture L is removed overhead and a mixture MN which comprises the essential proportion of EDA in the form of a high-boiling azeotrope with water and piperazine is drawn off via the bottom; and mixture MN is introduced into column 5-2 in which mixture M is drawn off overhead or via an upper side draw and mixture N is drawn off at the bottom or in a lower side draw.

6. The process according to claim 5, wherein the bottom temperature in column 5-1 is 170° C. or less and the bottom temperature in column 5-2 is 180° C. or more.

7. The process according to claim 5, wherein mixture M is not condensed and is introduced into the bottom or stripping section of column 5-1 in the form of vapors; and/or is introduced into an evaporator of the column 5-1 in the form of heating vapor.

8. The process according to claim 2, wherein the MEG which is introduced into stage 1 has a sulfur content of less than 100 ppm.

9. The process according to claim 8, wherein MEG which is to be introduced into stage 1 is first introduced into stage 2 or stage b), and mixture D separated off in stage b) is introduced into stage 1.

10. The process according to claim 1, wherein stream I from stage d) is separated in a further stage 4 into the following mixtures:
    (vi) a mixture J comprising DETA; and
    (vii) a mixture K comprising TEG.

11. The process according to claim 10, wherein stage 4 is conducted in a rectification column in which mixture J is drawn off overhead or from an upper side draw and mixture K is drawn off as the bottom product or from a lower side draw.

12. The process according to claim 1, wherein stage a) is conducted in a dividing wall column a-T in which mixture A is drawn off at the top of the dividing wall column; and in which mixture B is drawn off in a side draw of the dividing wall column between the top and bottom; and in which mixture C is drawn off at the bottom of the dividing wall column.

13. The process according to claim 12, wherein the rectification in the dividing wall column a-T is conducted at a pressure of 1 bar or less.

14. The process according to claim 1, wherein stage b) is conducted in a rectification column, where mixture D is preferably drawn off as a top product or at an upper side draw and mixture E is preferably drawn off as a bottom product or at a lower side draw.

15. The process according to claim 1, wherein stage c) is conducted in a rectification column, where mixture F is drawn off overhead or via an upper side draw and mixture G is drawn off via the bottom or a lower side draw.

16. The process according to claim 1, wherein stage d) is conducted in a rectification column, where mixture H is drawn off overhead or via an upper side draw and mixture I is drawn off as bottom product or via a lower side draw.

17. The process according to claim 1, wherein the triethylene glycol used in stage d) is used in an amount such that the molar ratio of TEG to DETA in mixture F after the TEG has been fed in is in the range from 1:1 to 10:1.

* * * * *